United States Patent [19]
Dandliker et al.

[11] Patent Number: 5,880,287
[45] Date of Patent: Mar. 9, 1999

[54] POLYOXYHYDROCARBYL RELATED PRODUCTS AND METHODS FOR FLUORESCENCE ASSAYS

[75] Inventors: Walter B. Dandliker, La Jolla; Robert Francis Devlin; Peter Olaf Gustaf Arrhenius, both of San Diego; Mao-Lin Hsu, Fountain Valley, all of Calif.

[73] Assignee: Hyperion, Inc., Miami, Fla.

[21] Appl. No.: 476,544

[22] Filed: Jun. 7, 1995

Related U.S. Application Data

[63] Continuation-in-part of Ser. No. 346,098, Nov. 29, 1994, and a continuation-in-part of Ser. No. 333,603, Nov. 2, 1994, which is a continuation of Ser. No. 701,465, May 15, 1991, abandoned, which is a continuation-in-part of Ser. No. 524,212, May 15, 1990, abandoned, said Ser. No. 346,098, is a division of Ser. No. 701,449, May 15, 1991, Pat. No. 5,403,928, which is a continuation-in-part of Ser. No. 524,212, May 15, 1990, abandoned.

[51] Int. Cl.$^6$ .......................... C09B 23/00; C07D 513/02
[52] U.S. Cl. ........................ 548/156; 548/219; 548/416; 548/427; 548/455; 564/275; 546/152; 8/659
[58] Field of Search ..................... 548/156, 416, 548/427, 219, 455; 8/659; 564/275; 546/152

[56] References Cited

U.S. PATENT DOCUMENTS

| | | | |
|---|---|---|---|
| 2,951,797 | 9/1960 | Sharp | 204/158 |
| 3,116,256 | 12/1963 | D'Alelio et al. | 252/301.2 |
| 3,287,470 | 11/1966 | Pugin et al. | 260/314.5 |
| 4,104,466 | 8/1978 | Tsuchida et al. | 342/433 |
| 4,404,355 | 9/1983 | Boguslaski et al. | 536/18.1 |
| 4,614,723 | 9/1986 | Schmidt et al. | 436/536 |
| 4,707,454 | 11/1987 | Hendrix | 436/546 |

(List continued on next page.)

FOREIGN PATENT DOCUMENTS

| | | |
|---|---|---|
| 0 260 298 | 9/1987 | European Pat. Off. . |
| 0336879 | 10/1989 | European Pat. Off. . |
| 0502723 | 9/1992 | European Pat. Off. . |
| 3215689 | 9/1988 | Japan . |
| 63-264674 | 11/1988 | Japan . |
| 9002747 | 3/1990 | WIPO . |

OTHER PUBLICATIONS

Castillo, "Bis (Metilsiloxi) Ftalocianinas Silicio (IV)," *Rev. Latinoamer. Quim.* 10:113–116 (1979).
Fukuda et al., Japanese Patent No. 62–249986 for "Porphyrin Derivative", *Patent Abstracts of Japan* 12(128):136 (1988).
Meyer et al., "Polymers with the Central Atom of a Macrocycle in the Main Chain. 1. Polycondensation reactions with phthalocyaninato silicon and hemiporphyrazinato germanium compounds," *Chemical Abstracts* 81:2 at abstract No. 152673g (1974).
Moser and Thomas (editors), *The Phthalocyanines*, CRC Press, Inc., Boca Raton, FL, vol. 1:123–127., 1990.
Sanwa Kagaku Kenkyusho, Japanese Patent No. J6 3215–689–A, *Derwent Publications* (1980) (Patent Abstract).
Sielcken et al., "Phthaloocyaninato Polysiloxanes Substituted with Crown Ether Moieties," *J. Amer. Chem. Soc.* 112(8):3086–3093 (1990).
Toyo Ink Manufacturing, Japanese Patent No. J6 3264–674–A, *Derwent Publications* (1980) (Patent Abstract).
Grant et al., eds., *Grant & Hack's Chemical Dictionary*, p. 241 (McGraw–Hill Book Company, Fifth Edition).
Leznoff et al., eds., *Phthalocyanines: Properties and Applications* 2:29–37 and 168–170 et al.
Meyer et al., "Polymere mit dem Zentralatom eines Makrocyclus in der Hauptkette; 4. Kovalenter Einbau von Aluminium–, Silicium– and Germaniumkomplexen des Phthalocyanins in Polester", *Die Angewandte Macromolekulare Chemie* 72:173–184 (1978).
Hartmann et al., "Polymere mit dem Zentralatom eines Macrocyclus inder Hauptkette, 2: Polykondensations–reaktionen mith Germaniumkomplexen des Phthalocyanin und meso–Tetraphenyloporphins", *Die Makromolekulare Chemie* 176:831–847 (1975).
Hartmann et al., "Polymers with the Central Atom of a Macrocycle in the Main Chain 2; Poly Condensation Reactions with Germanium Complexes of Phthalocyanine and Meso–Tetra–Phenylporphin", *Chemical Abstracts* 83:79669 (1975).
Meyer et al., "Polymers with the Central Atom of a Macrocycle in the Main Chain. 4. Covalent Incorporation of Aluminum, Silicon, and Germanium Complexes of Phthalocyanine in Polyesters", *Chemical Abstracts* 90(14):1 (1979).
Mashiko et al., "Porphyrins, Hydrioporphyrins, Azaporphyrins, Phthalocyanines, Corroles, Corrins and Related Macrocycles", Chapter 21.1 in _, pp. 813–898.
Moser and Thomas, eds., *The Phthalocyanines*, CRC Press, Inc., Boca Raton, FL, vol. 1:123–127.
Merck Index (Rahway, J.J., Merck & Co., 1989) p. 172.

*Primary Examiner*—Mukund J. Shah
*Assistant Examiner*—Pavanaram K. Sripada
*Attorney, Agent, or Firm*—Lyon & Lyon LLP

[57] ABSTRACT

Fluorescent dyes which are free of aggregation and serum binding are provided. These dyes are suitable for applications such as fluorescence immunoassays, in vivo imaging and in vivo tumor therapy. Fluorescence immunoassays methods are provided which use fluorescent dyes which are free of aggregation and serum binding. Such immunoassay methods are thus, particularly useful for the assay of biological fluids, such as serum, plasma, whole blood and urine. The present invention is directed to compositions comprising an oligonucleotide linked to a detectably labeled marker component comprising a fluorophore moiety which comprises a substantially planar, multidentate macrocyclic ligand coordinated to a central atom capable of coordinating with two axial ligands and two polyoxyhydrocarbyl moieties which are attached as axial ligands to the central atom. The present invention is also directed to nucleic acid hybridization and amplification methods employing such compositions.

17 Claims, 28 Drawing Sheets

U.S. PATENT DOCUMENTS

| | | | |
|---|---|---|---|
| 4,732,570 | 3/1988 | Baumgartner et al. | 8/506 |
| 4,822,733 | 4/1989 | Morrison | 435/6 |
| 4,822,877 | 4/1989 | Inada et al. | 540/145 |
| 4,849,207 | 7/1989 | Sakata et al. | 424/1.1 |
| 4,877,872 | 10/1989 | Morgan et al. | 540/145 |
| 5,053,423 | 10/1991 | Liu | 514/410 |
| 5,059,510 | 10/1991 | Jones et al. | 430/270 |
| 5,135,717 | 8/1992 | Renzoni et al. | 422/61 |
| 5,177,200 | 1/1993 | Kluger et al. | 540/122 |
| 5,403,928 | 4/1995 | Arrhenuis | 540/128 |

FIG. 7a.
| COMPOUND NAME | COMPOUND STRUCTURE | WAVELENGTH |
|---|---|---|
| 4-(4H-THIOPYRAN-4-YLIDENE-4-H-THIOPYRAN) | 05101  | λ726 (4.17) |
| QUINONE METHIDE, TRISPHENOQUINONE (A TRIQUINOCYCLOPROPANE) | 31212 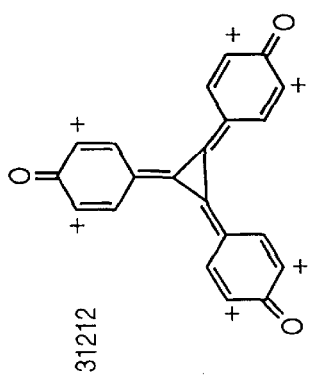 | λ769 (4.71) |
| 8-PHENYLAMINO-5-AMINO-2,3-DICYANO-1,4-NAPHTHOQUINONE | 32221 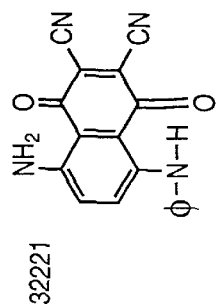 | λ758 (4.24) 735 (3.95), 786 (3.99). |
| 8-(4'METHYLPHENYLAMINO)-5-AMINO-2,3-DICYANO-1,4-NAPHTHOQUINONE | 32222 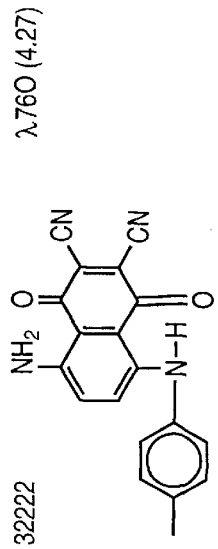 | λ760 (4.27) |

FIG. 7b.

| COMPOUND NAME | COMPOUND STRUCTURE | WAVELENGTH |
|---|---|---|
| 8-(4' METHOXYPHENYLAMINO)-5-AMINO-2,3-DICYANO-1,4-NAPHTHOQUINONE | 32223 | $\lambda$ 760 (4.27) |
| 8-(4' CHLOROPHENYLAMINO)-5-AMINO-2,3-DICYANO-1,4-NAPHTHOQUINONE | 32224 | $\lambda$ 758 (4.22) |
| 8-(4'-DIMETHYLAMINOPHENYLAMINO-5-AMINO-2,3-DICYANO-1,4-NAPHTHOQUINONE | 32225 | $\lambda$ 802 (4.28) |
| 1,4-DIAMINOANTHRAQUINONE-(N-m-hexyl)-3'-THIOXO-2,3-DICARBOXIMIDE | 33438 | $\lambda$ 763 |
| 1,4-DIAMINOANTHRAQUINONE-(N-m-octyl)-3'-THIOXO-2,3-DICARBOXIMIDE | 33439 | $\lambda$ 762 |

FIG. 7C.

| COMPOUND NAME | COMPOUND STRUCTURE | WAVELENGTH |
|---|---|---|
| ANTHRAQUINONE-1,4-DISULFENIC ACID | 34102 | λ 425 (3.82); 740 (3.66) (BASIC SOLN.) |
| ANTHRAQUINONE-1,5-DISULFENIA ACID | 34103 | λ 419 (3.92), 732 (3.79) (BASIC SOLN.) |
| ANTHRAQUINONE-1,4-DISELENIC ACID | 34105 | λ 439 (3.88), 742 (3.79) |
| 6,15-BIS(ANILIO) INDAUTHRENE | 35509 | λ 445-460 (4.12), 715 (4.48), 790 (4.74) |

FIG. 7d.
| COMPOUND NAME | COMPOUND STRUCTURE | WAVELENGTH |
|---|---|---|
| 8,17-DIPHENOXYINDAUTHRENE | 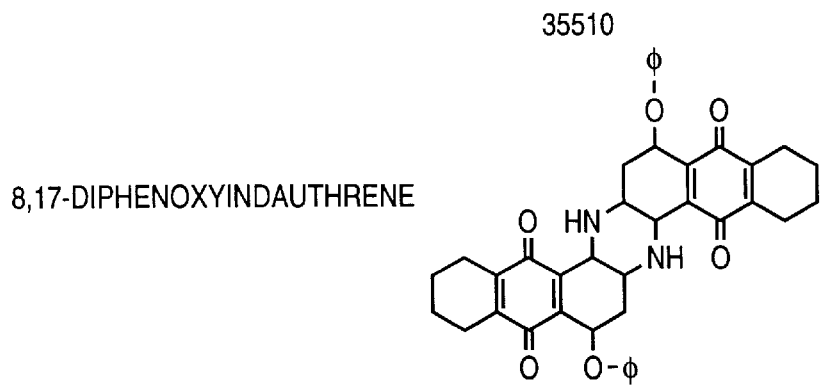 35510 | |
| 8,17-BIS(2-TOLUIDINO) INDANTHRENE | 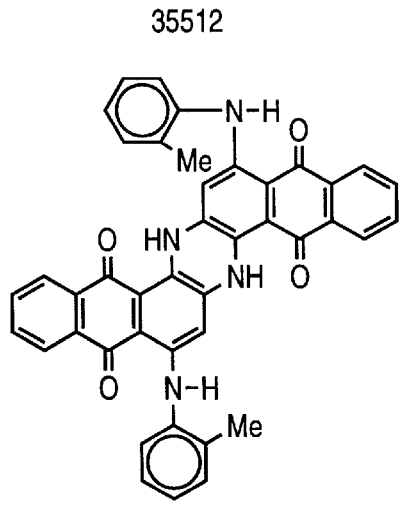 35512 | λ 715 (4.51), 785 (4.66) |
| 8,17-BIS(3-TOLUIDINO) INDANTHRENE | 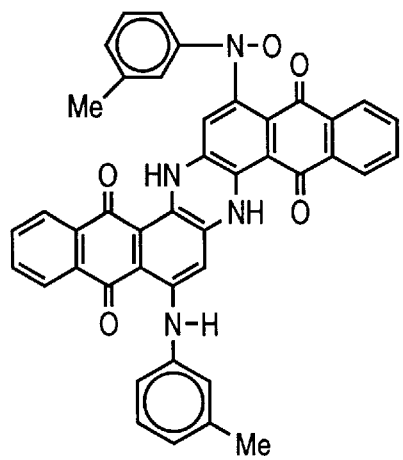 35513 | λ 455-466 (4.15), 715 (4.48), 790 (4.75) |

FIG. 7e.
| COMPOUND NAME | COMPOUND STRUCTURE | WAVELENGTH |
|---|---|---|
| 8,17-BIS(4-TOLUIDINO) INDANTHRENE | 35514 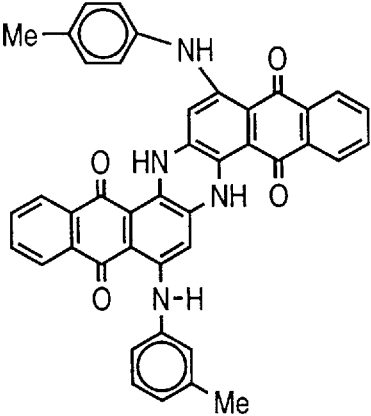 | λ 440-455 (3.94), 715 (4.27), 790 (4.49) |
| 8,17-BIS(2-TOLYLOXY) INDANTHRENE | 35515 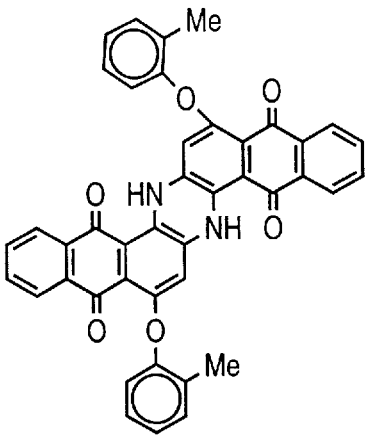 | λ 610 (4.03), 680 (4.39), 735 (4.47) |
| 8,17-BIS(PHENYLTHIO) INDANTHRENE | 35516 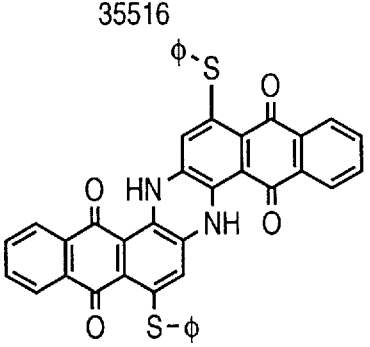 | λ 615 (4.01), 685 (4.40), 750 (4.60) |

FIG. 7f.

| COMPOUND NAME | COMPOUND STRUCTURE | WAVELENGTH |
|---|---|---|
| 8,17-BIS(2-ANISIDINO) INDANTHRENE | 35517 | λ 465 (3.99), 715-720 (4.45), 790 (4.63) |
| 8,17-BIS(3-ANISIDINO) INDANTHRENE | 35518 | λ 465-470 (3.98), 720-725 |
| 8,17-BIS(4-ANISIDINO) INDANTHRENE | 35519 | λ 465 (3.99), 715-720 (4.47), 790 (4.69) |

FIG. 7g.
| COMPOUND NAME | COMPOUND STRUCTURE | WAVELENGTH |
|---|---|---|
| 8,17-BIS(2-METHOXY-PHENOXY) INDANTHRENE | 35520 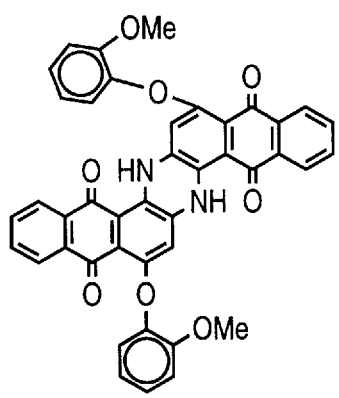 | $\lambda$ 610 (4.05), 675-680 (4.36), 735-740 (4.44). |
| 8,17-BIS(4-METHOXY-PHENOXY) INDANTHRENE | 35521 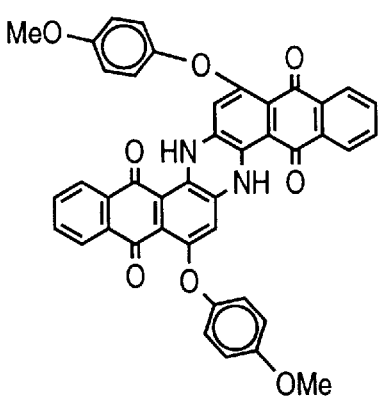 | $\lambda$ 610 (4.00), 675-680 (4.43), 735-740 (4.43). |
| 8,17-BIS(4-TOLYLTHIO) INDANTHRENE | 35522 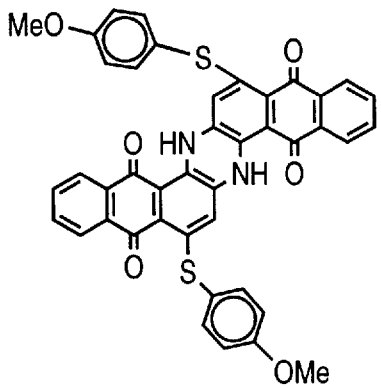 | $\lambda$ 615 (3.91), 685 (4.41), 750 (4.59). |

FIG. 7h.
| COMPOUND NAME | COMPOUND STRUCTURE | WAVELENGTHS |
|---|---|---|
| 8,17-BIS(4-ETHOXYANILINO) INDANTHRENE | 35523 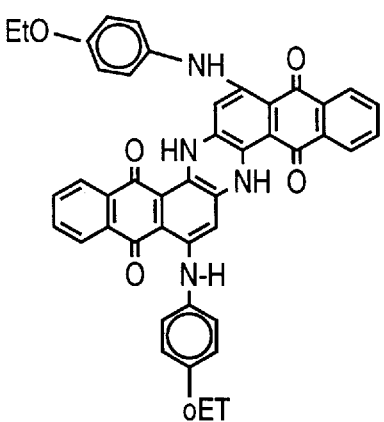 | λ 450-460 (3.96), 720 (4.40), 790 (4.53). |
| 8,17-BIS(2-CHLOROANILINO) INDANTHRENE | 35524 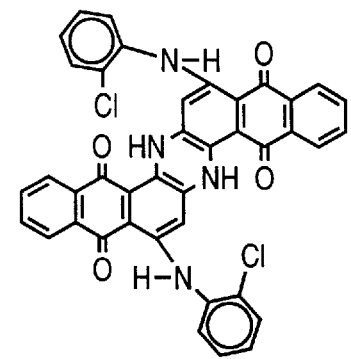 | λ 455 (4.03), 710-715 (4.49), 780 (4.62). |
| 8,17-BIS(3-CHLOROANILINO) INDANTHRENE | 35525 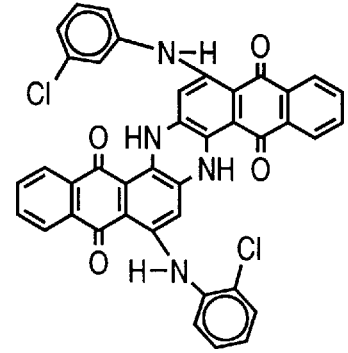 | λ 455 (3.81), 710-755 (4.10), 785 (4.36). |

FIG. 7i.
| COMPOUND NAME | COMPOUND STRUCTURE | WAVELENGTH |
|---|---|---|
| 8,17-BIS(4-CHLOROANILINO) INDANTHRENE | 35526 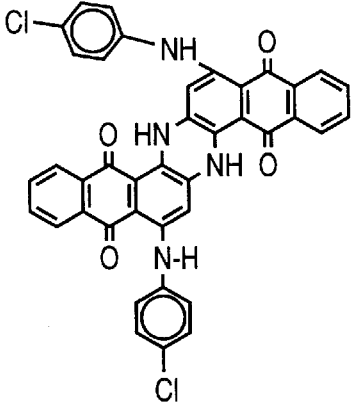 | λ 460 (3.92), 710-715 (4.21), 785 (4.32). |
| 8,17-BIS(4-CHLOROPHENOXY) INDANTHRENE | 35527 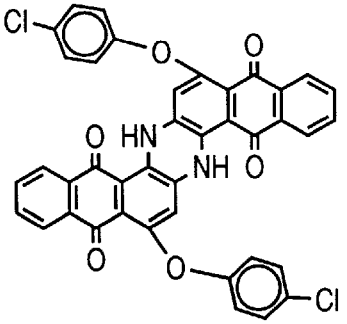 | λ 615 (4.21), 675 (4.45), 720-725 (4.54). |
| 8,17-BIS(2-METHYLTHIO-ANILINO) INDANTHRENE | 35528 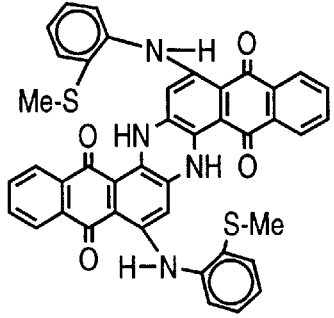 | λ 460 (4.04), 710-715 (4.46), 785 (4.68). |

FIG. 7j.

| COMPOUND NAME | COMPOUND STRUCTURE | WAVELENGTH |
|---|---|---|
| 8,17-BIS(3-METHYLTHIO-ANILINO) INDANTHRENE | 35529 | λ 460 (4.18), 710-715 (4.55), 790 (4.78). |
| 8,17-BIS(4-METHYLTHIO-ANILINO) INDANTHRENE | 35530 | λ 455 (4.15), 710-720 (4.55), 790 (4.78). |
| 8,17-BIS(2-METHOXYPHENYL-THIO) INDANTHRENE | 35531 | λ 615 (4.00), 685 (4.48), 750 (4.61). |
| 8,17-BIS(4-CHLORO-2-TOLUIDINO) INDANTHRENE | 35532 | λ 450 (3.96), 710-715 (4.41), 780 (4.49). |

FIG. 7k.

| COMPOUND NAME | COMPOUND STRUCTURE | WAVELENGTH |
|---|---|---|
| 8,17-BIS(PHENYLSULFONYL) INDANTHRENE | 35533 | $\lambda$ 610-615 (4.15) 675-685 (4.24), 700-730 (4.21). |
| 8,17-BIS(4-CHLOROPHENYL-THIO) INDANTHRENE | 35534 | $\lambda$ 615 (4.03), 685 (4.43), 750 (4.61). |
| 8,17-BIS(2-TOLYSULFONYL) INDANTHRENE | 35535 | $\lambda$ 615 (4.12), 675-685 (4.33), 705-715 (4.35). |

FIG. 71.
| COMPOUND NAME | COMPOUND STRUCTURE | WAVELENGTH |
|---|---|---|
| 8,17-BIS(4-TOLYSULFONYL) INDANTHRENE | 35536 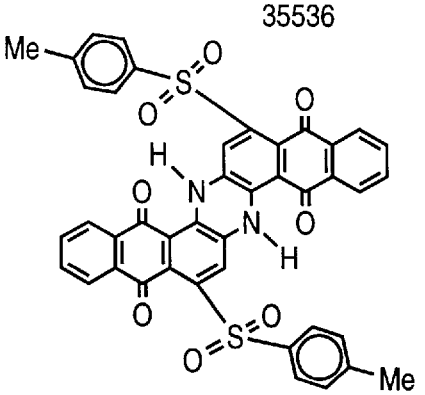 | λ 615 (412), 680-690 (4.33), 705-715 (4.34). |
| 8,17-BIS(4-BIPHENYLYL-AMINO) INDANTHRENE | 35537 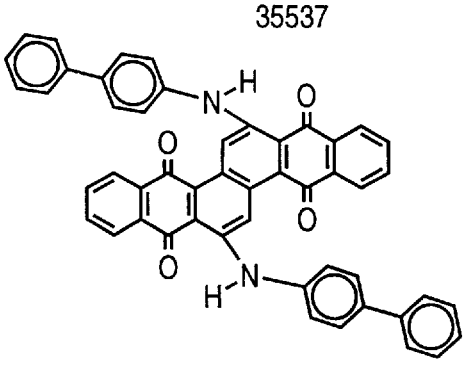 | λ 715 (4.42), 784-790 (4.52). |
| 8,17-BIS(4-CHLOROPHENYL-SULFONYL) INDANTHRENE | 35538 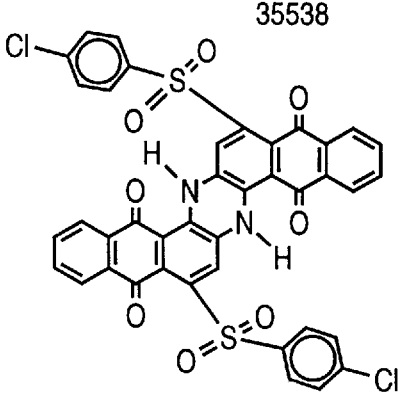 | λ 610 (4.17), 670-680 (4.24), 700-730 (4.21). |

FIG. 7m.
| COMPOUND NAME | COMPOUND STRUCTURE | WAVELENGTH |
|---|---|---|
| 2-ANILINO-3,4-PHTHALOYLACRIDONE | 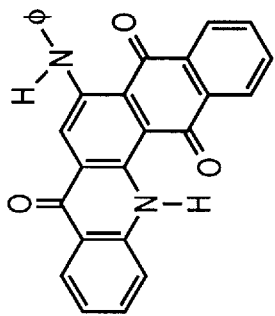 36509 | λ 721 (4.11) |
| 2-(4-ANISIDINO)-3,4-PHTHALOYLACRIDONE | 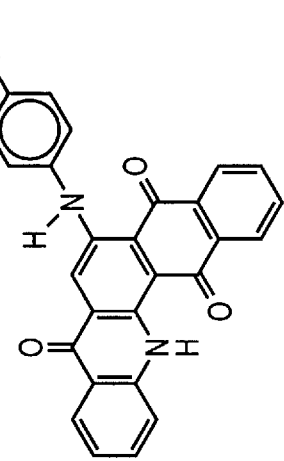 36511 | λ 732 (4.08) |
| PHENYLPHENYLVINYLMETHYLIUMCHLORIDE |  50017 | λ 758 (5.11) |

| COMPOUND NAME | COMPOUND STRUCTURE | | WAVELENGTH |
|---|---|---|---|
| (4-METHOXYPHENYL)-(4' METHOXY-PHENYLVINYL) METHYLIUM CHLORIDE | 50024  MeO–⌬–CH=⁺(CH=CH)₃–⌬–OMe | Cl⁻ | λ 725 (5.40) |
| (4-METHOXYPHENYL)-(4' METHOXY-PHENYLVINYL) METHYLIUM CHLORIDE | 50025  MeO–⌬–CH=⁺(CH=CH)₄–⌬–OMe | Cl⁻ | λ 792 (5.46) |
| (4-DIMETHYLAMINOPHENYL)-(4' DIMETHYLAMINOPHENYLVINYL) METHYLIUM CHLORIDE | 50032  (Me)₂N–⌬–CH=⁺(CH=CH)₂–⌬–N(Me)₂ | Cl⁻ | λ 790 |
| BINDSCHEDLER'S GREEN | 52001  (Me)₂N–⌬–N=⌬=⁺N(Me)₂ | Cl⁻ | λ 725 |
| TRIS (P-DIMETHYLAMINOPHENYL) AMMENIUM PERCHLORATE | 53151  (Me)₂N–⌬–⌬=⁺N(Me)₂ ... ⁺N–⌬–N(Me)₂ | ClO₄⁻ | λ 400 (4.3), 905 (4.5) |

FIG. 7n.

| COMPOUND NAME | COMPOUND STRUCTURE | WAVELENGTH |
|---|---|---|
| BIS (DIMETHYLAMINO) STREPTON POLYMETHINECYANINE | 61046 | λ 734 (5.55) |
| BIS-(4-DIMETHYLAMINOPHENYL)-STREPTOPOLYMETHINECYANINE | 61073 | |
| 1,1,3,3,-TETRAKIS (P-DIMETHYLAMINOPHENYL)-2-PROPENOL PERCHLORATE z | 61211 | λ 740 (4.5) |
| 1,1,5,5,-TETRAKIS (4-DIMETHYLAMINO-PHENYL)-2,4-PENTADIENOL PERCHLORATE | 61212 | λ 810 (5.2) |

FIG. 70.

| COMPOUND NAME | COMPOUND STRUCTURE | WAVELENGTH |
|---|---|---|
| 3,3'-DIETHYL-2,2'-THIADICARBON CYANINE IODIDE | 62303 | $\lambda$ 653 (5.4) |
| 3,3'-DIETHYL-2,2'-THIATRICARBON CYANINE BROMIDE (IODIDE) [PERCHLORATE] | 62401, (62403a) [62403b] | $\lambda$ 757, Br⁻, $\lambda$763 (5.32) $\tilde{\omega}$(I), $\lambda$773 [5.32] [ClO₄] |
| 3,3'-DIMETHYL-2,2'-THIATRICARBON CYANINE IODIDE | 62402 | $\lambda$ 752 (5.38) |
| 3,3'-DIETHYL-5,5'-DICHLORO-11-CIPHENYLAMINO-10,12-ETHYLENE-THIATRICARBOCYANINE PERCHLORATE | 62411 | $\lambda$ 823 (5.19) |

FIG. 7p.

| COMPOUND NAME | COMPOUND STRUCTURE | WAVELENGTH |
|---|---|---|
| 3,3'-DIETHYL-2,2'-OXATRICARBON CYANINE IODIDE | 62703 | λ 687 (5.40) |
| 1,1'-DIETHYL-2,2'-QUINOTRICARBON CYANINE IODIDE | 64005 | λ 818 |
| 1,1'-DIETHYL-4,4'-QUINOTRICARBON CYANINE IODIDE (CRYPTOCYANINE) | 64102 | λ 710 (5.41) |
| 1,1'-DIETHYL-11-BROMO-4,4'QUINON DICARBOCYANINE BROMIDE | 64104 | λ 795 |
| 1,1',1''-TRIETHYL-11-(4'QUINOYL)-4,4'-QUINODCARBOCYANINE DIIODIDE | 64106 | λ 770 |

FIG. 7q.

| COMPOUND NAME | COMPOUND STRUCTURE | WAVELENGTH |
|---|---|---|
| 1,1'3,3,3'3'-HEXAMETHYL-2,2'-INDOTRICARBOCYANINE IODIDE (HITC) | 64303a (C f.51144) (64O3b-ClO₄⁻) | λ 741 (5.38) |
| 1,1'3,3,3'3'-HEXAMETHYL-4,5,4'5'-DIBENZO-2,2-INDOTRICARBON CYANINE PERCHLORATE | 64304 | λ 782 (5.27) |
| 3,3,3',3'-TETRAMETHYL-1,1'-BIS(4-SULFOBUTYL)-4,5,4'5'-DIBENZO-2,2'-INDOTRICARBON CYANINE, SODIUM SALT (IR-125) | 64311 | λ 795 (5.29) |
| IR-144 | 64312 | λ 745 (5.09) |

FIG. 7r.

| COMPOUND NAME | COMPOUND STRUCTURE | WAVELENGTH |
|---|---|---|
| | 65212 | $\lambda$ 766 (5.48) |
| 2-(2-ETHOXYETHENYL)-4,6-DIPHENYLPYRILIUM PERCHLORATE | 66001 $\phi$—⟨pyrilium⟩—CH=CH(OEt), $\phi$, ClO$_4^-$ | $\lambda$ 725 (3.95) |
| 2-(2-HYDROXYETHENYL)-4,6-BIS(METHYLPHENYL) PYRILIUM PERCHLORATE | 66002 Me-$\phi$—⟨pyrilium⟩—CH=CHOH, $\phi$-Me, ClO$_4^-$ | $\lambda$ 726 (3.03) |
| 2-(2-ETHOXYETHENYL)-4,6-BIS(BENZYL) PYRILIUM PERCHLORATE | 66004 $\phi$-CH$_2$—⟨pyrilium⟩—CH=CH(OEt), $\phi$-CH$_2$, ClO$_4^-$ | $\lambda$ 726 (3.42) |

FIG. 7S.

FIG. 7t.
| COMPOUND NAME | COMPOUND STRUCTURE | WAVELENGTH |
|---|---|---|
| 2-(2-HYDROXYETHENYL)-4,6-BIS(4-METHOXYPHENYL) PYRILIUM PERCHLORATE | 66005 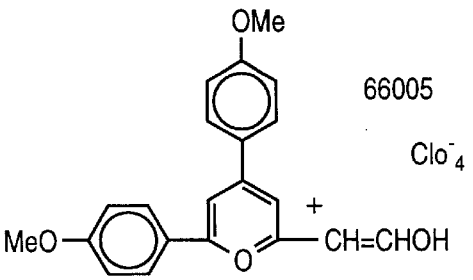 | λ 724 (3.54) |
| 2-(2-HYDROXYETHENYL)-4,6-BIS(4-ETHOXYPHENYL) PYRILIUM PERCHLORATE | 66008 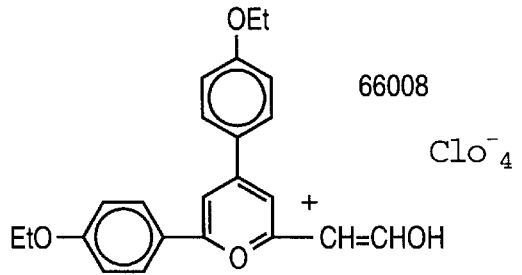 | λ 723 (3.20) |
| 2-(2-ETHOXYETHENYL)-4,6-BIS(4-METHOXYPHENYL) PYRILIUM PERCHLORATE | 66009 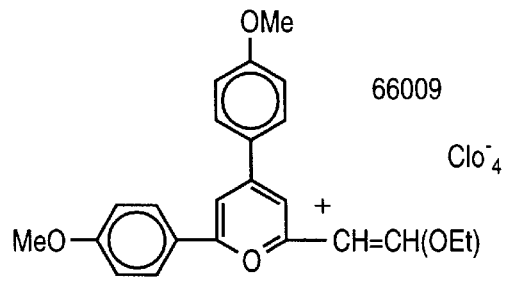 | λ 725 (3.77) |
| 2-(2-ETHOXYETHENYL)-4,6-BIS(ETHOXYPHENYL) PYRILIUM PERCHLORATE | 66013 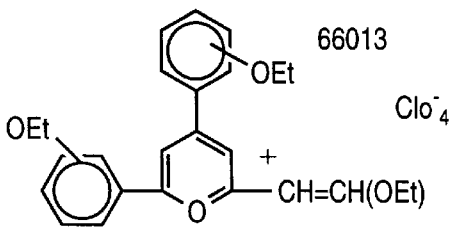 | λ 723 (3.60) |
| 2-(2-HYDROXYETHENYL)-4,6-BIS(2,4-DIMETHOXYPHENYL) PYRILIUM PERCHLORATE | 66014 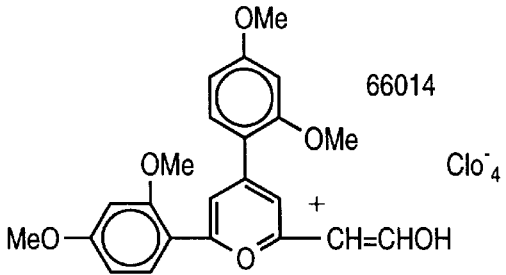 | λ 723 (3.00) |

| COMPOUND NAME | COMPOUND STRUCTURE | WAVELENGTH |
|---|---|---|
| 2-(2-ETHOXYETHENYL)-4,6-BIS(DIMETHOXYPHENYL) PYRILIUM PERCHLORATE | 66015 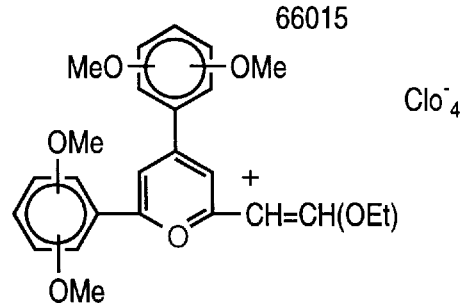 ClO$_4^-$ | λ 725 (3.01) |
| | 66204 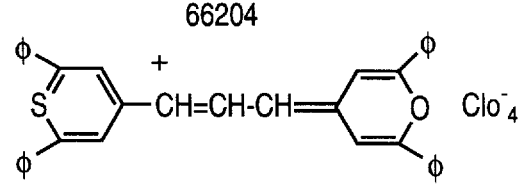 ClO$_4^-$ | λ 725 |
| | 66206 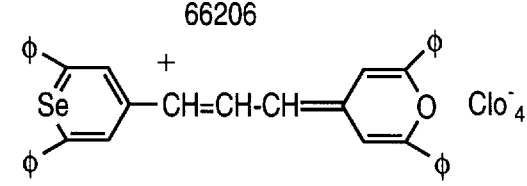 ClO$_4^-$ | λ 743 |
| | 66210 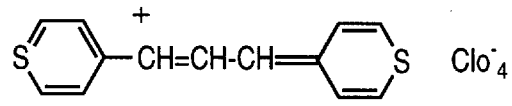 ClO$_4^-$ | λ 751 |
| | 67102 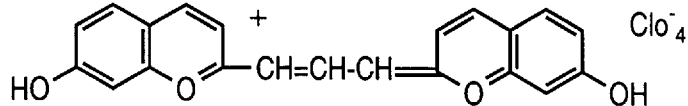 ClO$_4^-$ | λ 745 (4.60) |
FIG. 7u.

FIG. 7v.
| COMPOUND NAME | COMPOUND STRUCTURE | WAVELENGTH |
|---|---|---|
| 67422 | 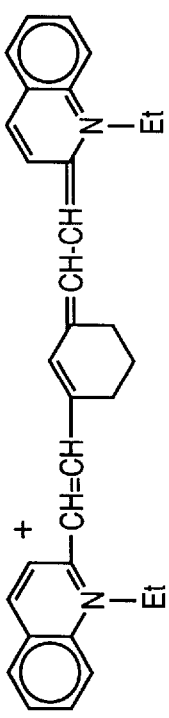 | λ 827 (5.41) |
| SQUARYLIUM DYE | 91022 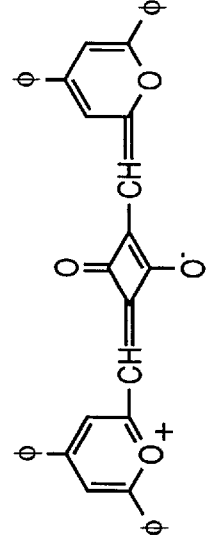 | λ 815 (4.79), 910 (4.82) |

POLYOXYHYDROCARBYL RELATED PRODUCTS AND METHODS FOR FLUORESCENCE ASSAYS

RELATED APPLICATIONS

This application is also a continuation-in part of U.S. patent application Ser. No. 08/346,098, filed Nov. 29, 1994, which is a divisional of U.S. patent application Ser. No. 07/701,449, filed May 15, 1991, (now U.S. Pat. No. 5,403, 928) which was a continuation-in-part of U.S. patent application Ser. No. 07/524,212, filed May 15, 1990, now abandoned.

This application is also a continuation-in part application of U.S. patent application Ser. No. 08/333,603, filed Nov. 2, 1994, which is a continuation of U.S. patent application Ser. No. 07/701,465, filed May 15, 1991, now abandoned, which was a continuation-in-part of U.S. patent application Ser. No. 07/524,212, filed May 15, 1990, now abandoned.

All of the above applications are incorporated herein by reference in their entirety including any drawings.

FIELD OF THE INVENTION

The present invention relates to the field of assays, in particular fluorescence immunoassays, receptor assays, and hybridization assays.

BACKGROUND OF THE INVENTION

The determination of the presence or amount of substances is commonly performed by immunoassay. Immunoassay techniques are based on the binding of the antigenic substance being assayed (the "target analyte") to a receptor for the target analyte. The term "analyte" or "target analyte" refers to the compound to be measured in an assay which may be any compound for which a receptor naturally exists or can be prepared which is mono- or polyepitopic, antigenic or haptenic, a single or plurality of compounds which share at least one common epitopic site or a receptor. Immunoassay methods can be applied to the assay of many different biologically active substances. Among such substances are haptens, hormones, gamma globulin, allergens, viruses, virus subunits, bacteria, toxins such as those associated with tetanus and animal venom, and many drugs. Similar techniques can be used in non-immunological systems with, for example, specific binding proteins.

Many different types of immunoassays are known in the art, including competitive inhibition assays, sequential addition assays, direct "sandwich" assays, radioallergosorbent assays, radioimmunosorbent assays and enzyme-linked immunosorbent assays. The basic reaction underlying most immunoassays is the binding of certain substance, termed the "ligand" or "analyte", by a characteristic protein (receptor) to form a macromolecular complex. These binding processes are reversible reactions, and the extent of complex formation for particular analyte and receptor concentrations is regulated by an equilibrium constant according to the law of mass action. Thus, at equilibrium, some of the analyte always exists unbound (free).

The measurement of target analytes in biological fluids, such as serum, plasma and whole blood, requires immunoassay methods which are both specific and sensitive. Both the specificity and sensitivity of an immunoassay depend on the characteristics of the binding interaction between the target analyte and the receptor involved. For example, the reaction must be specific for the analyte to be measured and the receptor used should not bind to any other structurally related compounds. In addition, by choosing a receptor with a high affinity for the target analyte, the sensitivity can be increased. The label used to monitor the assay also affects the sensitivity of an immunoassay. Either the target analyte or the receptor may be labeled to permit detection. Labels currently used for immunoassay of target analytes in biological fluids include radioisotopes (radioimmunoassay, RIA), enzymes (enzyme immunoassay, EIA), fluorescent labels (fluorescence immunoassay, FIA), and chemiluminescent labels (chemiluminescent immunoassay, CIA). Theoretically, fluorometry is capable of being one of the most sensitive of all analytic tools as it is possible to detect single photon events.

FIAs use fluorescent molecules as labels and may be either heterogeneous or homogeneous. Fluorescent molecules (fluorophores) are molecules which absorb light at one wavelength and emit light at another wavelength. See Burd, J. F., "Fluoroimmunoassay—Application to Therapeutic Drug Measurement," in P. Moyer et al., *Applied Therapeutic Drug Monitoring*, American Association of Clinical Chemistry (1984). Typically, an excitation pulse of radiation is directed onto or into a sample, followed by fluorescence of the sample, and the detection of the fluorescence radiation. Fluorescence is a phenomenon exhibited by certain substances, which causes them to emit light, usually in the visible range, when radiated by another light source. This is not reflection, but creation of new light. Current commercially available assay methods use fluorescein, which emits green light when radiated by a light source containing blue light. In addition to fluorescing, fluorescein (and other fluorophores) emit polarized light. That is, the light emitted has the same direction of polarization as the incident polarized light, if the fluorescein molecule is held fixed with its transition moment parallel to the electric field of the excitation.

Using a fluorescent polarizing probe in a competitive binding immunoassay provides a type of FIA called a fluorescence polarization immunoassay (FPIA). In this type of assay, the smaller the molecule is, the smaller its rotational relaxation time and the faster it rotates. Typically, antibody molecules are much larger than drug or drug-probe molecules. One advantage of the polarization technique is the elimination of a step to separate unbound probe. Although the unbound tracer is not physically eliminated from the samples in FPIA, its contribution is readily assessed by the polarization. Another advantage in the FPIA technique is lack of dependence on intensity. Unlike most assays using a light measurement, in which it is the intensity of the light that is correlated to drug concentration (so any variations in source light intensity will directly affect the sensitivity of the assay), the sensitivity of FPIAs is independent of intensity variations. Conventional FPIAs require separate measurements of both blank and sample.

One problem which has plagued fluorescence immunoassays has been discriminating the fluorescent signal of interest from background radiation. The intensity of signal from background radiation may be up to 10,000 times larger than the intensity of the fluorescent signal of interest. The problem of background detection is particularly pronounced in assay of biological samples. Many of the current fluorescence assays use the fluorescent molecule, fluorescein. Fluorescein has an excitation maximum of 493 nm, and there are numerous substances in biological fluids with overlapping excitation and emission similar to fluorescein. For example, in the analysis of blood plasma, the presence of a naturally occurring fluorescable material, biliverdin, causes substantial background radiation. Such compounds are highly fluorescent and contribute significant background signals which interfere with the label's signal, thus limiting the sensitivity of assays using fluorescein labels.

Two factors commonly viewed as going hand in hand and contributing to the problem background radiation are: (1) solvent sensitivity and (2) non-specific binding. Solvent sensitivity refers to tendency of a solvent to affect the fluorescent signal of the dye. For example, several dyes that are fluorescent in organic solvents tends to aggregate in agneous solutions and therefore exhibit quenched fluorescence. Non-specific binding refers to the tendency of sample components to interfere with the fluorescent signal of the dye. For example, serum components such as HSA often bind to conventional fluorescent dyes and quench or enhance interfere with the fluorescent signal.

It has been recognized that for analysis of biological fluids, it would be desirable to use a dye or label which is excitable at radiations of wavelengths of greater than background radiation. However, even though the background fluorescence of serum falls off at wavelengths approaching 600 nm, significant interference persists until 650 nm or greater. Previous attempts to create dyes of such wavelengths have been unsuccessful. See, e.g., Rotenberg, H. and Margarfit, R., *Biochem. Journal* 229:197 (1985); and D. J. R. Laurence, *Biochem. Journal* 51:168 (1952). Fluorescent dyes having emission wavelengths which reduce interference from background fluorescence include cyanines, porphyrins and azaporphyrins. However, it has been found that the use of such labels in fluorescence assays is limited by the problems of solvent sensitivity (significantly decreased fluorescence intensity in the aqueous assay solution in comparison to dimethylformamide) and non-specific binding to biological materials (significantly decreased fluorescence intensity in purified or isolated sample comparison to a sample containing serum components such as HSA).

Use of fluorophores having long decay times is especially important in techniques such as transient state assays where there is a need for fluorophores whose emissions may be measured over a time period of up to about 20 nanoseconds. It has been found that for fluorophores natural lifetime and extinction coefficient vary antibatically (i.e., when one increases, the other decreases; although they need not change at rates inversely to each other). Also, fluorophores having longer fluorescent lifetimes are more apt to be deactivated. Accordingly, fluorophores having enhanced decay times, i.e. having decay times which approach their natural lifetime, offer greater quantum yields and, thus, greater sensitivity.

Earlier attempts to overcome the problem of background radiation have involved: (1) the use of filters to reject detected radiation at all but a narrowly defined wavelength band; (2) binding fluorescent probes to a macro-molecular support thereby minimizing the effect of serum proteins while allowing detection of the binding to a target analyte, (see U.S. Pat. No. 4,615,986, issued Oct. 7, 1986); and (3) the use of chemical groups designed to improve the functional properties of the dyes (see Mujumdar, et al. Bioconjugate Chemistry 4: 105–110, 1993).

Arnost et al., U.S. Pat. No. 4,886,744, issued Dec. 12, 1989 ("Arnost") describes a fluorescent label with an unsymmetrical cyanine dye of structure:

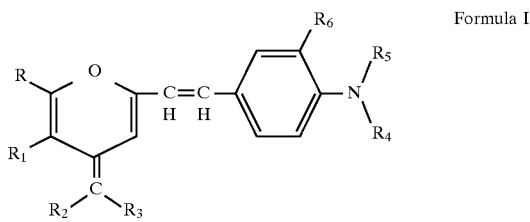

Formula I

Certain of the R groups can be "a hydrophilic group". Hydrophilllic groups are defined as including a variety of possibilities, including a polyether, in order to decrease aggregation and non-specific binding. The data set forth by Arnost are said to show that some of the "hydrophilic groups" decrease the nonspecific binding somewhat and lowered the binding constants from 7E5 down to 1.5E4, a factor of less than 50. The components of Arnost, et al. typically have an excitation maximum of less than 500 nm.

SUMMARY OF THE INVENTION

The present invention relates to marker components, fluorescent probes, oligonucleotides, hybridization assays, and immunoassays using such products and methods for making such products. According to the present invention, detectably labeled marker components are provided that comprise a fluorophore moiety coupled to one or more polyoxyhydrocarbyl moieties. The polyoxyhydrocarbyl moieties preferably reduce or remove the problems of solvent sensitivity and non-specific binding.

Use of such detectable labels or marker components in immunoassays is advantageous in that these labels have substantially the same intensities of parallel and perpendicular components of transient state fluorescence emission in the presence and absence of biological fluids such as serum. Thus, assay methods using these labels are capable of detecting low concentrations of target analyte in biological fluids.

These marker components may be used as labels for labeling an analyte, antigen, antibody or other molecule. These marker components may be optionally functionalized so as to include a linker arm which allows the marker component to be linked to the analyte, antigen, antibody or other molecule. A variety of linker arms which are suited to this purpose have been described. Kricka, J. J.; *Ligand-Binder Assays; Labels and Analytical Strategies*; pages 15–51; Marcel Dekker, Inc., New York, N.Y. (1985). The marker component is linked to the analyte, antigen, antibody or other molecule using conventional techniques.

In one aspect the present invention provides a detectably labeled marker component which comprises: (1) a fluorophore moiety comprising a luminescent substantially planar molecular structure having excitation wavelengths of at least about 500 nm and (2) coupled thereto one or more polyoxyhydrocarbyl moieties. Examples of preferred fluorophores, polyoxyhydrocarbyl moieties, and linkages of the two are described in detail herein. In addition, evidence is provided demonstrating the effectiveness of the marker components at reducing solvent sensitivity and non-specific binding.

In especially preferred embodiments, the marker components of the present invention can be used to make probes as generally described in commonly owned U.S. application Ser. No. 08/051,446, filed Apr. 21, 1993, and used in immunoassays as generally described in commonly owned U.S. application Ser. No. 08/035,633, filed Mar. 23, 1993, the disclosure of both of which are incorporated herein by reference in their entirety, including any drawings.

BRIEF DESCRIPTION OF THE DRAWINGS

FIG. 7 shows additional examples of dyes that can be used in the present invention. The compound numbers correspond to those used in Organic Colorants, Okawara, et al., 1986, incorporated herein by reference in its entirety including any drawings.

DETAILED DESCRIPTION OF THE INVENTION

Figure 1:
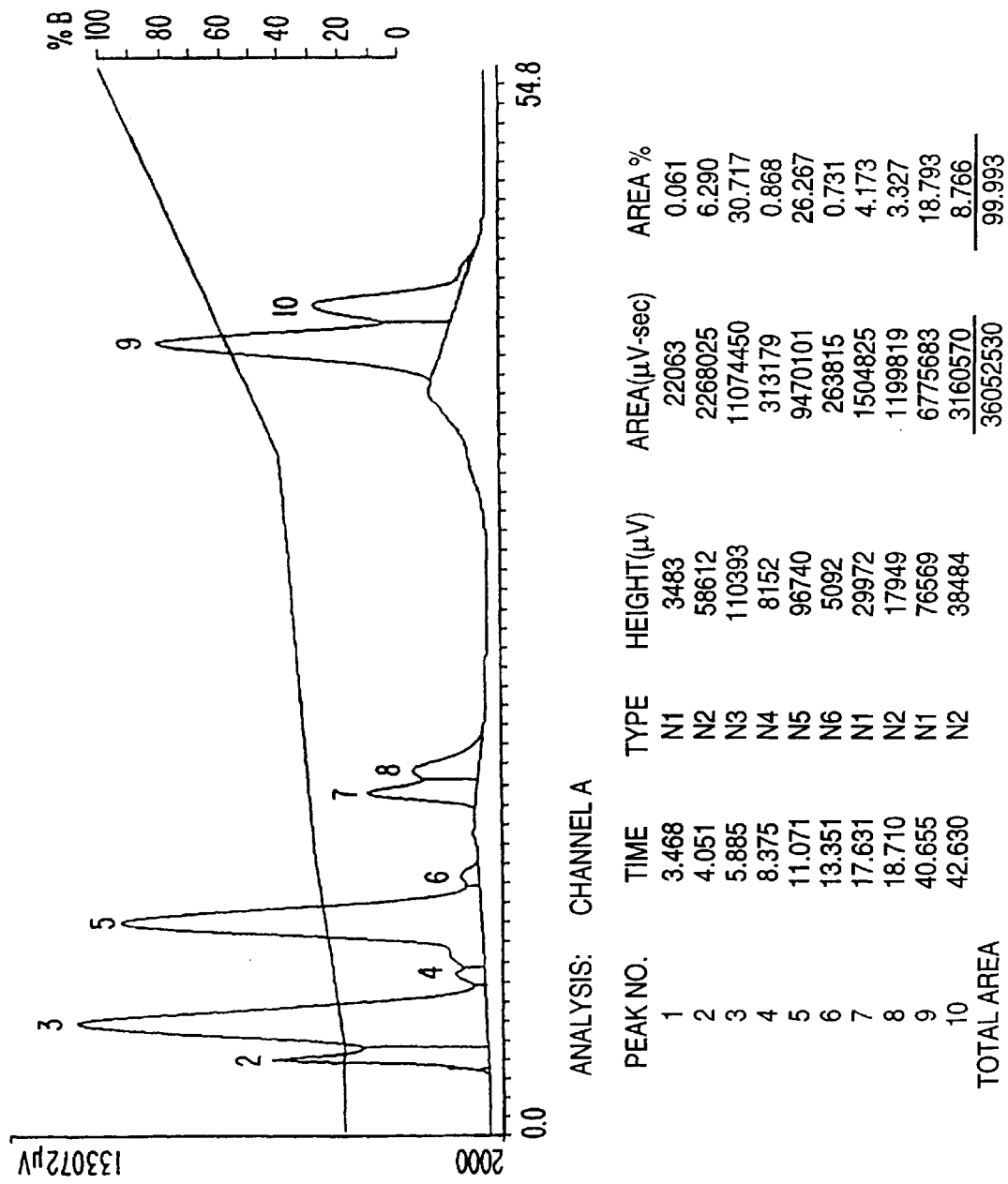
FIG. 1 is a RPHPLC elution diagram of a reaction carried out in 0.1M, pH 9.3 carbonate buffer between bis-reactive CY5.5 and PEG-amine. Non-specific binding was absent in Peaks 9 and 10.
Figure 2:
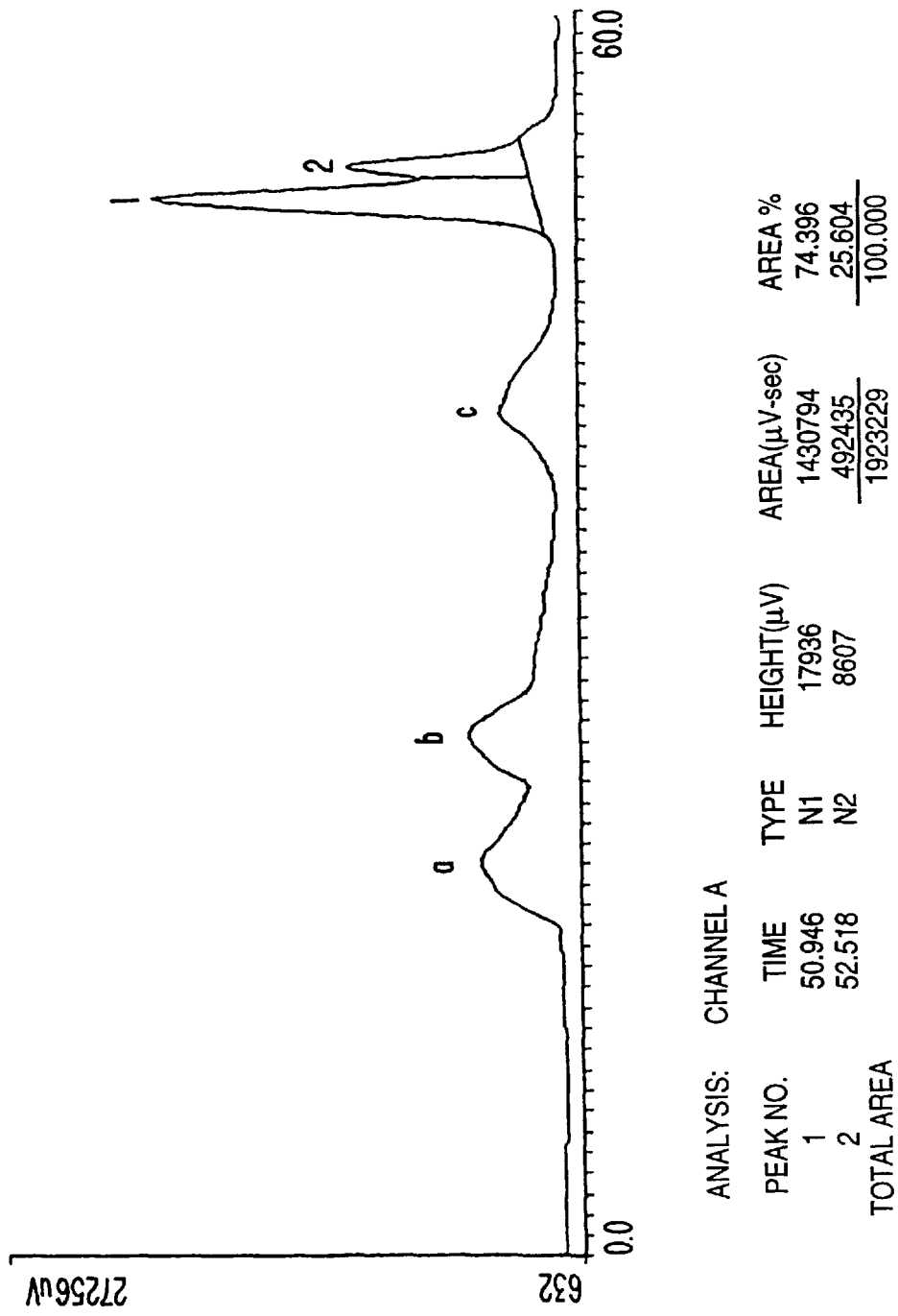
FIG. 2 is similar to FIG. 1 except that the reaction was carried out under anhydrous conditions in a mixture of DMF and NMP. Peaks a, b and c all showed strong non-specific binding whereas non-specific binding was absent for peaks 1 and 2.
Figure 3:
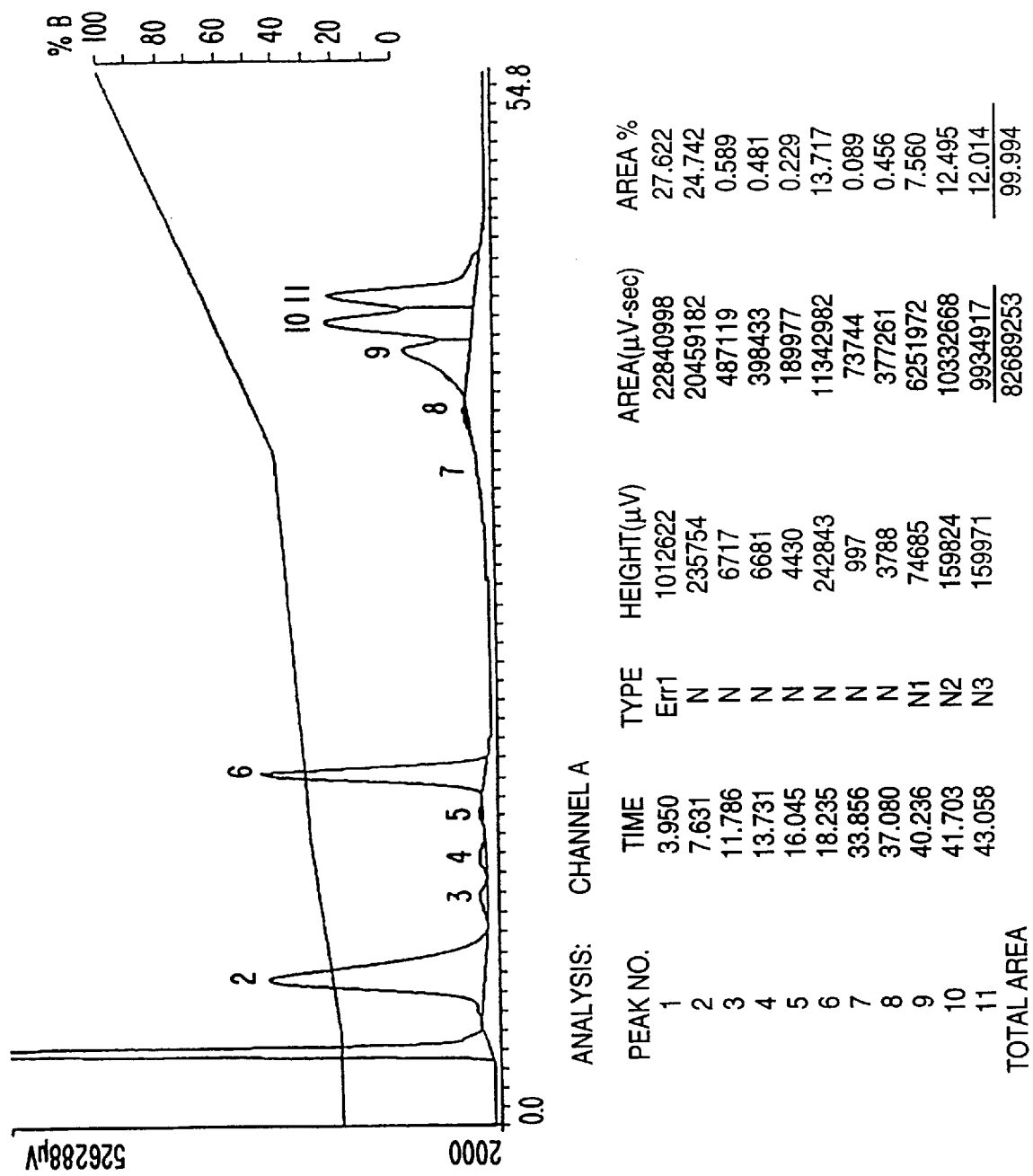
FIG. 3 is a RPHPLC elution diagram of the same reaction mixture as in FIG. 2 except after removal of DMF and NMP by rotary evaporation and vacuum drying.
Figure 4:
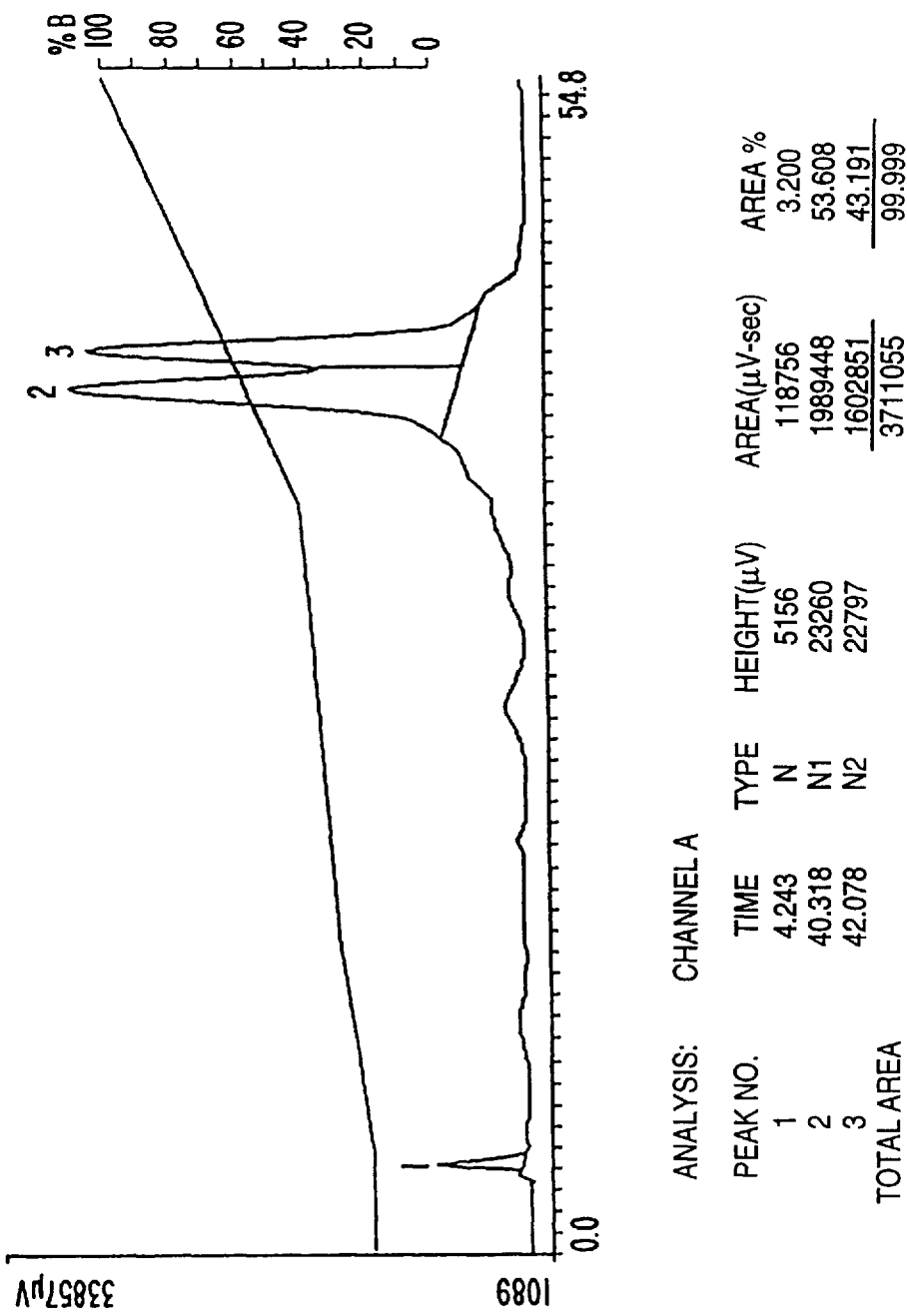
FIG. 4 is a RPHPLC elution diagram of a fast moving peak in the separation on Biogel P-6.
Figure 5:
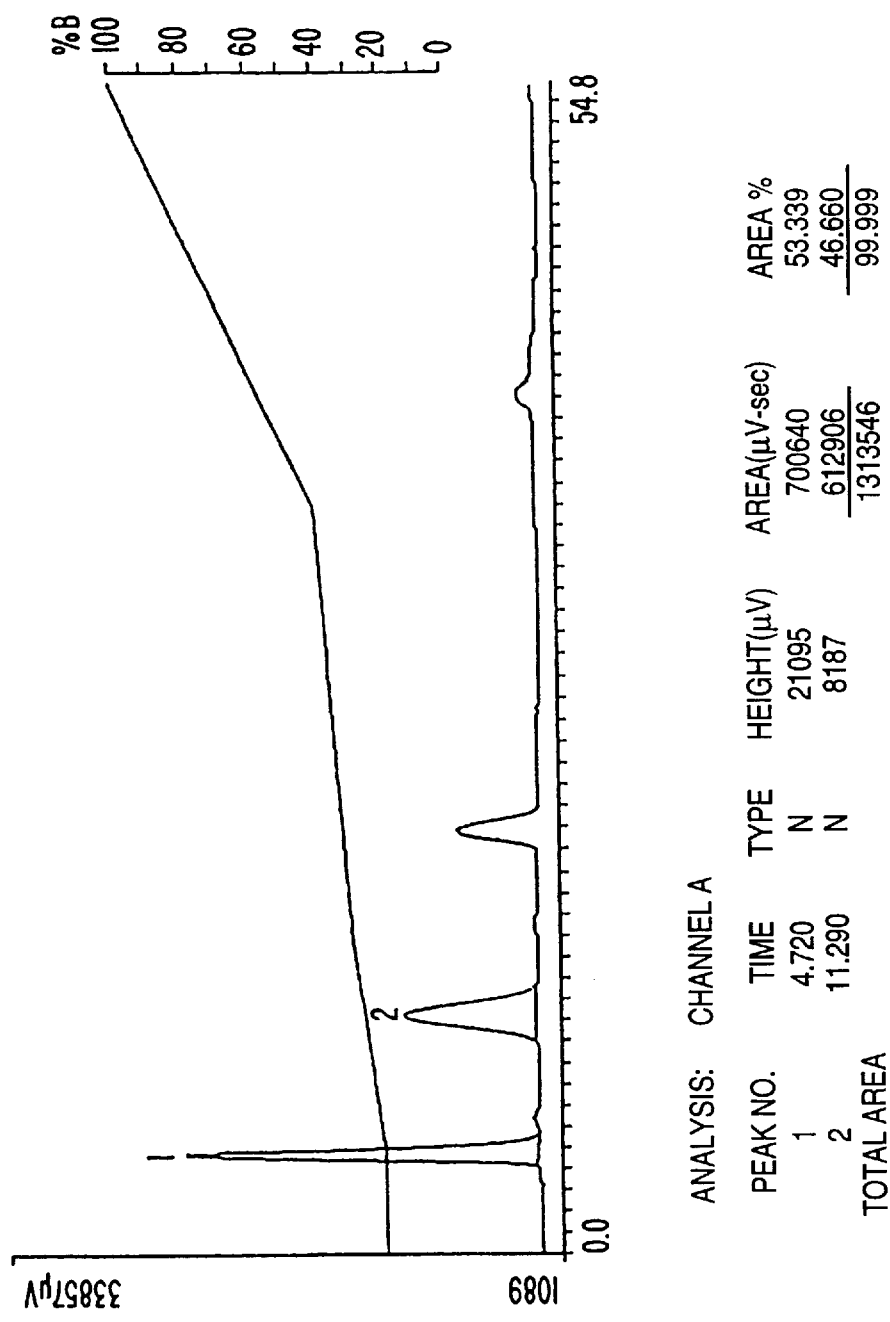
FIG. 5 is similar to FIG. 4 except for the slow moving peak from P-6 separation.
Figure 6:
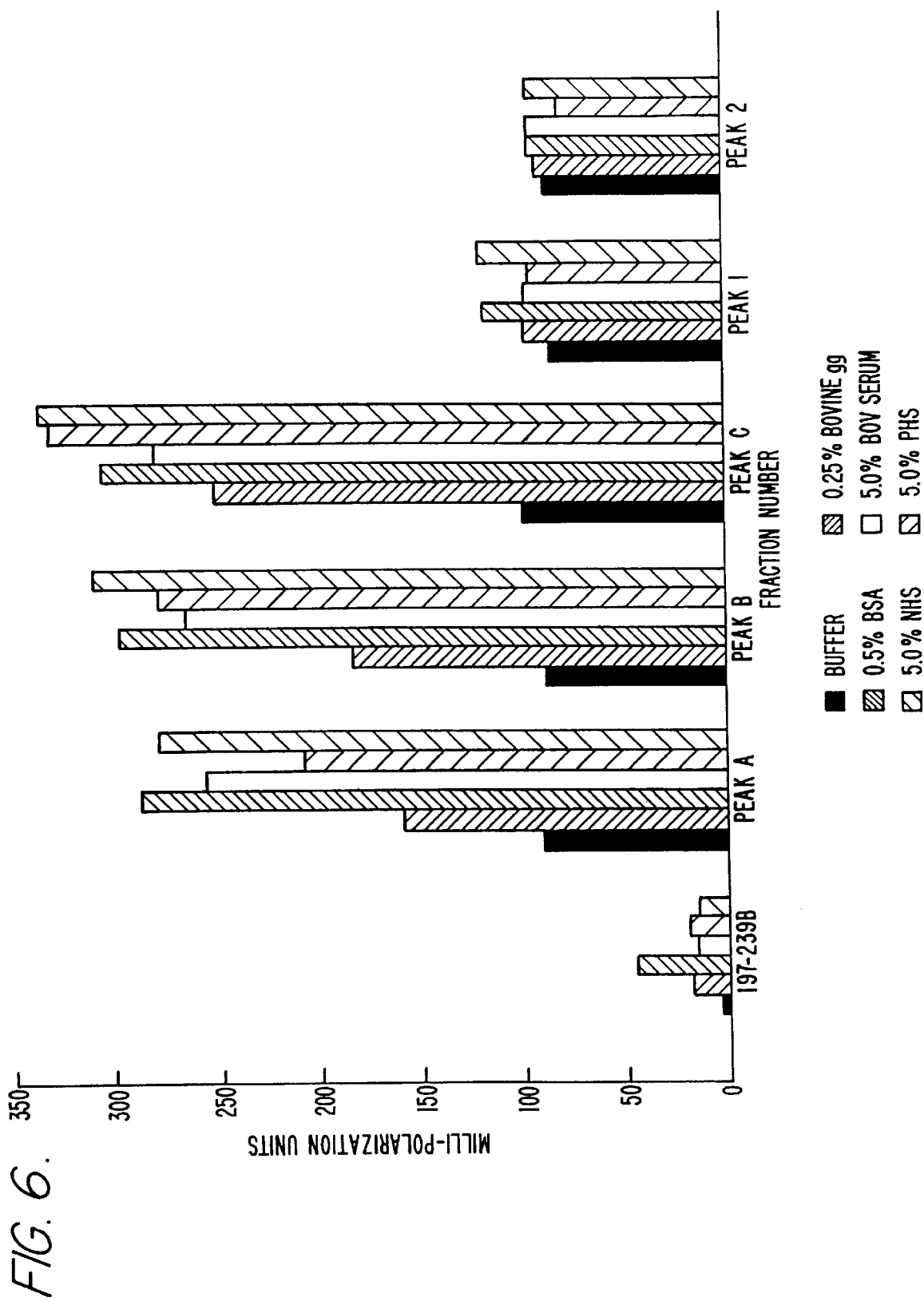
FIG. 6 shows the behavior of the RPHPLC fractions from reaction mixture 199-146A (reaction in DMF+NMP) when tested with a panel of sera or serum components to reveal non-specific binding. Polarization of the transient state fluorescence served as the index of non-specific binding. As a reference, data for an especially preferred dye of the present invention termed La Jolla Blue are also shown. The first bar in each group gives the polarization of the dye or fraction in question as observed in buffer alone (TDx buffer). The data shows that Peaks A, B and C (corresponding to a, b, and c, respectively, in FIG. 2) bind strongly when run with the test panel while La Jolla Blue, Peak 1 (FIG. 2), and Peak 2 (FIG. 2) show negligible binding. The differences between the polarizations of La Jolla Blue (197 239B), Peak 1 and Peak 2 in buffer alone are a reflection only of the differences in the photophysical properties of the different dyes structures and are not associated with aggregation or the presence or absence of non-specific binding. Thus it can be seen that CY 5.5 after reaction with PEG-amine is virtually free of non-specific binding and that Peaks a, b and c correspond to various forms of bare, unprotected dye while Peaks 1 and 2 are coupled to PEG.

The following description includes preferred modes of carrying out the invention and is made for the purpose illustrating the general principles of the invention rather than limiting the invention in any manner.

I. PREFERRED MARKER COMPONENTS

A. Preferred Fluorophore Moieties

Accordingly, in general, preferred are fluorophores which efficiently produce fluorescence upon excitation with light whose wavelength falls in the range of about 200 to about 1000 nanometers, preferably in the range of about 600 to 800 nanometers more preferably the range above 650 nm. Suitable fluorophores include those which absorb and/or emit at wavelengths which are distinguishable from the excitation and emission maxima of other solution components (such as proteins present in a sample) to minimize background fluorescence.

Since these marker components are particularly useful in assays using samples of biological fluids, for those uses, preferred are fluorophores having excitation and/or emission wavelengths of at least about 500 nanometers which reduces interference from the ambient fluorescence of other sample components. Some samples, such as serum, may exhibit considerable interfering background fluorescence from flavins, flavoproteins, NADH, etc. when excitation wavelengths less than 500 nm are used.

For certain applications, such as fluorescence polarization immunoassays, preferred fluorophores may also exhibit a high degree of fluorescence polarization when bound and a low degree of polarization when bound. For certain applications such as fluorescence transient state assays, preferred fluorophores are also characterized by measured fluorescence decay times in the range of about 1 nanosecond to about 50 nanoseconds, preferably in the range of about 5 to about 20 nanoseconds. For other applications, such as phosphorescent labels, fluorophores having even longer decay times may be used. The term "decay time" is the time which must elapse in order for the concentration of excited molecules to decrease from its initial concentration to 1/e of that value.

Thus, preferred are fluorophores which produce fluorescent light efficiently, i.e., which are characterized by high absorbtivity at the appropriate wavelength and high fluorescence quantum yields. For certain applications, preferred fluorophores have measured fluorescence decay times on the order of at least 2 nanoseconds and exhibit a high degree of fluorescence polarization.

Suitable fluorophore moieties comprise a luminescent substantially planar molecular structure. One class are fluorophore moieties in which the luminescent substantially planar molecular structure comprises a substantially planar macrocyclic multidentate ligand which coordinates a central atom which may coordinate with two axial ligands, one on either side of the macrocyclic ligand (i.e. having a trans orientation). The term "axial ligand" refers to a substituent which, together with a macrocyclic ligand, forms a coordination complex with a central atom. The axial ligand lies normal to the plane described by the macrocyclic ligand.

Preferred central atoms are elements which may form octahedral coordination complexes containing two ligands with a trans or axial orientation, on either side and perpendicular to the planar macrocyclic ligand. For use as fluorescent marker components in certain applications the central atom should not have too high atomic number (about 30 or less) so that fluorescence is largely lost by transition to the triplet state. For uses such as in vivo tumor therapy, higher atomic weight atoms may be used, or in separation-type assays or for phosphorescent labels. For use as marker components in fluorescence immunoassays, suitable central atoms are those to which may coordinate two axial ligands and which are not of high enough atomic number to cause extensive fluorescence quenching by transition to the triplet state. Preferred elements for the central atom include silicon, germanium, phosphorus, and tin, especially preferred are silicon and germanium.

Preferred multidentate ligands include nitrogen-containing macrocycles which have conjugated ring systems with pi-electrons. These macrocycles may be optionally substituted, including substitution on bridging carbons or on nitrogens. Suitable macrocycles include derivatives of porphyrins, azaporphyrins, corrins, sapphyrins and porphycenes and other like macrocycles having conjugated π-electron ring systems. In view of the fact that they incorporate many of the above-noted characteristics, an especially preferred class of macrocycles comprise porphyrin derivatives, and azaporphyrin derivatives (porphyrin derivatives wherein at least one of the bridging carbons is replaced by a nitrogen atom). Azaporphyrin derivatives include derivatives of mono-, di- and triazaporphyrin and porphyrazine. These macrocycles may optionally have fused aromatic rings. These azaporphyrin derivatives include phthalocyanine, benzotriazaporphyrin and naphthalocyanine and their derivatives. The preparation and fluorescent qualities of many of these compounds are known and some are available commercially. Moser, F.; *Phthalocyanine Compounds*; Reinhold Publishing Co., New York (1963); Wilkinson, G. (editor); *Comprehensive Coordination Chemistry*; Volume 2, pages 813–898; Pergamon Press, New York (1987); Hanack, M., et al.; "Synthesis and Properties of a New Kind of One-Dimensional Conductor", *Journal of Organometallic Chemistry* 204:315–325 (1981); and Lezhoff, C. C. and Lever, A. S. P. (editors); *Phthalocyanines: Properties and Applications*; VCH Publishers, Inc., New York (1989).

Other classes of fluorophores to which one or more polyoxyhydrocarbyl groups may be attached according to this invention are indicated in the examples and FIG. 7 below.

For certain applications, such as fluorescence polarization assays, preferred macrocycles are azaporphyrin derivatives which exhibit a high degree of polarization, that is, those which emit strongly polarized light. For these applications, preferred are macrocycles having lower degrees of symmetry, preferably having lower symmetry than $D_{4h}$. One preferred group includes macrocycles having at least one fused aromatic ring or peripheral substituent. Thus, preferred macrocycles include azaporphyrin derivatives having fused aromatic rings at positions which result in decreased symmetry. Preferred classes of azaporphyrin derivatives comprise derivatives of monoazaporphyrin, diazaporphyrin, and triazaporphyrin having lower than $D_{4h}$ symmetry.

Preferred fluorophores include: (1) polymethine dyes; (2) quinoid dyes; (3) indanthrene dyes; (4) indigoid dyes; (5) azines, such as Nile Blue A and laser dyes); (6) arylmethane dyes and heterocyclic analogs; (7) pyrylium, thiopyryilum, and squarylium dyes; (8) quinone methides; (9) conjugated betaine dyes (derivatives of pyridinium N-cyclopentadienide); and (10) macrocycles such as porphyrins, hydroporphyrins, azaporphyrins including phthalocyanines, corroles, corrins and pentapyrrole macrocycles such as sapphyrins. Examples of such dyes are provided below.

Polymethine dyes include symmetrical and unsymmetrical cyanines either of which can be cationic, anionic or neutral cyanines (merocyanines). The structures of the groups terminating the polymethine chain determines into which of the above classes a particular cyanine falls.

The longest wavelength of absorption is determined by both the terminal groups and the number of —CH═CH— groups in the polymethine chain. Substitution along the polymethine chain can produce either red shifts or blue shifts depending upon the structure of the substituent group and its position in the chain.

Other structural modifications can be made by cyclization or by coupling structures together. Hence, it can be appreciated that the number of cyanines possible is very large. Thousands of these compounds have been synthesized in the search for better photographic sensitizers.

Especially preferred fluorophores include: (1) aryl terminated polymethine dyes, such as trimethines, pentamethines, and heptamethines; (2) quinoid dyes such as 1-Amino-2-benzoyl-4-(arylamino)anthraquinones, 6-(Arylamino)napth[2,3,c]acridan-5,8,14-triones; (3) indanthrene dyes; (4) 1,4-diaminoanthraquinone-2,3-dicarboxamides; (5) tetraaminoanthraquinones; (6) azine dyes; (7) pyrylium, thiopyryilum and squarylium dyes; and (8) naphthoquinone methides.

B. Preferred Polyoxyhydrocarbyl Moieties

Preferred solubilizing polyoxyhydrocarbyl moieties include water soluble carbohydrates such as glucose, sucrose, maltotriose and the like; water soluble carbohydrate derivatives such as gluconic acid and mannitol, and oligosaccharides; polypeptides such as polysine and naturally occurring proteins; and water soluble polymers such as polyvinylpyrrolidone, poly(vinyl alcohol), poly (ethylenimine), polyacrylic acid, polyacrylamide, ethylene oxide copolymers such as Pluronic™ (a polyether) and Tetronic™ (BASF) polyol surfactants and, in particular, polyethers such as other polyoxyalkylenes including poly (ethylene glycol), or other water soluble mixed oxyalkylene polymers, and the like.

A particularly preferred class of solubilizing polyoxyhydrocarbyl moieties comprises poly(ethylene glycol) (PEG) and poly(ethylene glycol) derivatives, such as poly(ethylene glycol) monomethyl ether. Other suitable PEG derivatives include PEG-silicon derived ethers. Many of these polymers are commercially available in a variety of molecular weights. Others may be conveniently prepared from commercially available materials, such as by coupling of an amino-PEG to a haloalkyl silyl or silane moiety. When linked to a fluorophore moiety, these polyoxyhydrocarbyl moieties impart particularly advantageous qualities of solubility in aqueous solution with improved measured fluorescence decay time, and improved fluorescence intensity. Moreover, the resulting marker components are water soluble and show decreased non-specific binding, especially decreased binding to serum albumin which has heretofore been a problem with certain fluorophores, particularly porphyrin or phthalocyanine dyes which have been functionalized with groups such as sulfonate to impart increased water solubility to the molecule. Non-specific binding of fluorophore or marker component impairs the accuracy of the resulting immunoassay. These marker components which comprise fluorophore linked to PEG may also exhibit improved fluorescence intensity in aqueous solution with decreased quenching.

Suitable PEGs may vary in molecular weight from about 200 to about 20,000 or more, more preferably 2,000 to 20,000, more preferably 4,000 to 15,000, most preferably 8,000 to 10,000. Choice of a particular molecular weight may depend on the particular fluorophore chosen and its molecular weight and degree of hydrophobicity, as well as the particular application for which the fluorophore-PEG complex is to be used.

C. Absorbance and Polarization Behavior of Preferred Marker Components

The lack of solvent sensitivity and non-specific binding to HSA and serum components was demonstrated by measurement of absorbance spectra and transient state fluorescence emission. Marker components which comprise a central atom (for example, silicon) coupled to one or more polyoxyhydrocarbyl moieties such as PEG may be sensitively characterized by measurements of transient state fluorescence. In such measurements the intensity of the two components polarized either parallel or perpendicular to the direction of polarization of the exciting pulse is monitored over a time period equal to about 3 times the decay time of the marker component. Such curves reflect extinction coefficient, quantum yield, decay time and state of polarization and supply sensitive indications on the chemical and physical condition of the marker component.

For example, if the excited state is being deactivated or converted to the triplet state the overall intensities are lowered and the decay times shortened. If the rotary brownian motion of the molecule is being altered by an increase in viscosity or by being bound to a large molecule, the ratio of the intensity of the parallel to the perpendicular component is increased. The term "bound" refers to the condition in which a binding interaction has been formed between a molecule and its specific binding partner.

Some marker components according to the present invention show, within experimental error of about 5%, the same intensities, decay time and polarization in DMF (an organic solvent) as in SAP (saline azide phosphate, an aqueous neutral buffer). To some extent these properties are shared by other marker component preparations. A distinctive and important property of the marker components of the present invention is an insensitivity to (and lack of binding to) the components in serum which is evidenced by a lack of any measured effect of serum on the intensities, decay time or relative magnitudes of the polarized components of the fluorescence. This property is crucial for the marker components to be useful for applications such as assays using biological materials.

The absorbance spectra in the visible and near-infrared range for a product of hydroxy silicon phthalocyanine with PEG monomethyl ether of average molecular weight 350 show that the positions and heights of the absorbance maxima are nearly identical in DMF, an organic solvent and in SAP (saline azide phosphate), an aqueous buffer solution. In contrast, silicon phthalocyanine which is unsubstituted with the solubilizing polyoxyhydrocarbyl axial ligands would be nearly insoluble in either of these solvents and would exhibit only very low absorbance levels in DMF and virtually none in SAP.

Transient state fluorescence emission for the same PEG-substituted silicon phthalocyanine as used above show that emission was virtually unaffected by the addition of human serum to sample in SAP. A silicon phthalocyanine solubilized by derivatization of the phthalocyanine macrocycle with sulfonate without the PEG ligands would show changes in both fluorescence intensity and polarization when serum was added. Those changes are abrogated by the replacement of the hydroxy groups with the PEG axial ligands.

Transient state fluorescence emission for a PEG-substituted silicon phthalocyanine where the phthalocyanine macrocycle is sulfonated demonstrated the same transient state emission in the presence of HSA, and HSA plus serum, as it did in buffer alone (SAP). Sulfonation of the macrocycle did not affect the ability of the axial polyoxyhydrocarbyl solubilizing moieties to prevent nonspecific binding of the marker component to either HSA or serum components.

Transient state fluorescence emission for a sulfonated silicon phthalocyanine which does not have any solubilizing polyoxyhydrocarbyl moieties linked to the central silicon atom in DMF shows the two components polarized either parallel or perpendicular with respect to the polarization of the excitation flash to be about equal. Transient state fluorescence of the same material in SAP at the same concentration shows that the material is solvent sensitive and that its fluorescence is about 40% quenched in SAP. The addition of serum to the solution produced an enhancement of fluorescence and induced polarization of the emission of this dye such that the parallel and perpendicular components were not of substantially equal intensity. This indicates substantial binding of the sulfonated silicon phthalocyanine to serum components. The change in intensity after addition of the serum is also indicative of binding to serum components.

Visual and near-infrared absorbance of a sulfonated silicon phthalocyanine in DMF show wavelength maxima and absorbances are 673 nm (0.634) and 603 nm (0.107) respectively. The absorption spectrum of the sulfonated silicon phthalocyanine in SAP at the same concentration show wavelength maxima and absorbance are 678 nm (0.509) and 606 nm (0.092), respectively.

II. PREPARATION OF PREFERRED MARKER COMPONENTS

According to one method of preparing the referred marker components of the present invention, the appropriate fluorophore moiety having hydroxy or halide groups as axial ligands is reacted with a reactive form of the solubilizing polyoxyhydrocarbyl moiety in a ligand exchange reaction according to the general reaction scheme:

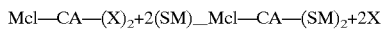

wherein Mcl denotes the macrocyclic ligand, CA the central atom, X the displaced ligand and SM the solubilizing moiety. This reaction may be carried out neat or, if desired, in solvent. Suitable solvents include quinoline, THF, DMF, imidazole and the like. Suitable reaction temperatures may vary, depending on the nature of the macrocyclic starting material and the solubilizing group. The reaction is generally complete in about 2 minutes to about 24 hours. The reaction mixture can be conveniently heated under reflux or by means such as a sand bath. For convenience, the reaction may be carried out at ambient pressure.

It is believed that this reaction takes place in two steps, with one polyoxyhydrocarbyl group coordinating as an axial ligand at a time. The reaction of the polyoxyhydrocarby moiety with the central atom coordinated macrocyclic ligand may proceed in stages. Products of the reaction of PEG with dihydroxy silicon phthalocyanine (PcSi(OH)$_2$) were observed. At the first stage ("Early Blue Stage"), the fluorophore moiety (SiPc), while being rendered soluble in both DMF and SAP (aqueous saline azide phosphate buffer), was markedly sensitive to solvent and was about 85% quenched. Product of the latter stage of the reaction ("Blue Green Product"), in contrast, was totally insensitive to solvent and showed the same emission intensity and decay time in either solvent.

Preferred synthetic methods are provided in example 5 of commonly owned U.S. Pat. No. 5,403,928, issued Apr. 4, 1995.

III. UTILITY

The marker components of the present invention are useful as fluorescent labels for fluorescent probes and in fluorescence immunoassays and also in as labels for in vivo imaging and in vivo tumor therapy. These marker components may be advantageously used as fluorescent labels in conventional fluorescence immunoassays, including fluorescence polarization immunoassays. When so used, these marker components may be linked to one member of a specific binding pair ("labeled binding partner") or an analog of such a member. The marker component may be directly attached or conjugated thereto or attached or conjugated via a linker arm. The term "specific binding pair"

refers to two different molecules (or compositions) wherein one of the molecules has an area on the surface or in a cavity which specifically recognizes and binds to a particular spatial and polar organization of the other molecule or molecular complex involving other molecules. The term "binding partner" refers to a molecule or molecular complex which is capable or specifically recognizing or being recognized by a particular molecule or molecular complex.

These labeled binding partners are useful in assays having a variety of formats, such as assays which involve competition for analyte or analyte binding partner (if a labeled analyte or analyte-analog as used) and may be used in either homogeneous or heterogeneous assays. In view of their advantageous freedom from aggregation in aqueous solution and lack of solvent sensitivity (indicating no detectable aggregation) in combination with their lack of nonspecific binding to serum components and other biological macromolecules, these markers are especially suited for use in assays for detecting an analyte in a sample containing a biological fluid such as serum. Thus, these marker components may be used as labels for fluorescent probes for detecting analytes in solutions where non-specific binding by serum components would severely compromise sensitivity of an assay, affecting both its accuracy and precision.

Alternatively, these marker components may be used as agents for in vivo imaging. When used as imaging agents, these marker components are conjugated to one member of a specific binding pair to give a labeled binding partner. The labeled binding partner is introduced into an animal. If the other member of the specific binding pair is present, the labeled binding partner will bind thereto and the signal produced by the marker component may be measured and its localization identified.

These marker components may also be used in in vivo tumor therapy. For example, photodynamic therapy involves using the marker component as a photosensitizing agent. The marker component (fluorescent label) is conjugated to a binding partner which may specifically recognize and bind to a component of a tumor cell. The localized triplet emission from the bound marker component conjugate after excitation by light, causes chemical reactions and selective damage and/or destruction to the tumor cells.

To assist in understanding the present invention, the following examples are included which describe the results of a series of experiments. The following examples relating to this invention should not, of course, be construed in specifically limiting the invention and such variations of the invention, now know or later developed, which would be within the purview of one skilled in the art are considered to fall within the scope of the invention as described herein and herein after claimed.

EXAMPLES

Dyes of the phthalocyanine, the porphyrin and the cyanine or polymethine classes have been coupled to one or more polyoxyhydrocarbyl groups, e.g., PEG (polyethylene glycol). In every case the presence of the polyoxyhydrocarbyl group(s) resulted in a dramatic decrease in the tendency to aggregate and even more importantly in the tendency to bind non-specifically to biological materials, (human serum or human serum components in the actual experiments).

We have compared bare unprotected dyes to those coupled to polyoxyhydrocarbyl groups in the mix-and-read assay for digoxin in the presence of serum or whole blood. In this assay protection of the fluorescent label (a phthalocyanine) is absolutely essential for achieving the sensitivity needed to monitor digoxin levels in patients under digoxin therapy. A probe made with a bare phthalocyanine would be useless for any practical application. The digoxin assay which is presently dominant in the therapeutic drug assay market utilizes a bare dye (fluorescein) in the probe. However, in order to perform the assay a separate, off-line precipitation and centrifugation must first be done to denature and remove serum constituents which would otherwise make the assay impossible.

We have outlined methods for engineering diverse classes of IR/near IR dyes which have photophysical parameters suggesting their usefulness as fluorescent probes. The reactions shown below indicate how various dyes could be engineered to eliminate aggregation and nonspecific binding. Similar schemes can be written to convert such engineered dyes into useful probes by attachment of the appropriate hapten, antibody or other biomolecule.

Example 1

Aryl-terminated polymethine dyes

Aryl-terminated polymethine dyes that can be coupled to one or more polyoxyhydrocarbyl moieties include those described in W. B Tuemmler, B. S. Wildi, *J. Org. Chem.* 1958, 80, 3772–3777; R. Wizinger, G. Renckhoff, *Helv. Chim. Acta* 1941, 24, 369E-388E; and H. Lorenz, R. Wizinger, *Helv. Chim. Acta* 1945, 28, 600–612, all of which are incorporated herein by reference in their entirety, including any drawings. Aryl-terminated polymethine dyes that can be coupled to one or more polyoxyhydrocarbyl moieties are preferably of the structure:

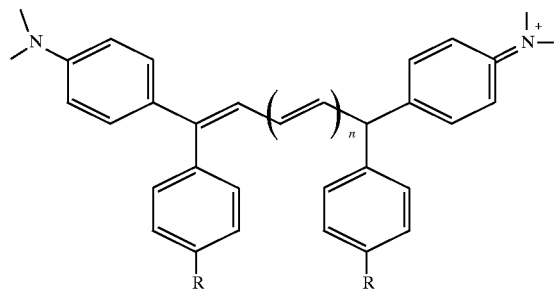

wherein n is 0, 1, or 2 and R is H, Cl, or $N(CH_3)_2$.

Aryl-terminated polymethine dyes of the above structure have the following spectral properties:

| R | n | $\lambda_{max}$ (nm) | ε |
|---|---|---|---|
| H | 0 | 755 | 100,000 |
| H | 1 | 833 | 208,000 |
| H | 2 | 935 | 195,000 |
| Cl | 0 | 770 | 100,000 |
| Cl | 1 | 845 | 187,000 |
| Cl | 2 | 942 | 151,000 |
| $N(CH_3)_2$ | 0 | 740 | 36,000 |
| $N(CH_3)_2$ | 1 | 809 | 183,000 |
| $N(CH_3)_2$ | 2 | 911 | 186,000 |

The aryl-terminated polymethine dyes of the above structure can be synthesized as described in W. B Tuemmler, B. S. Wildi *J. Org. Chem.* 1958, 80, 3772–3777. For example, trimethines (n=0) can be synthesized as follows:

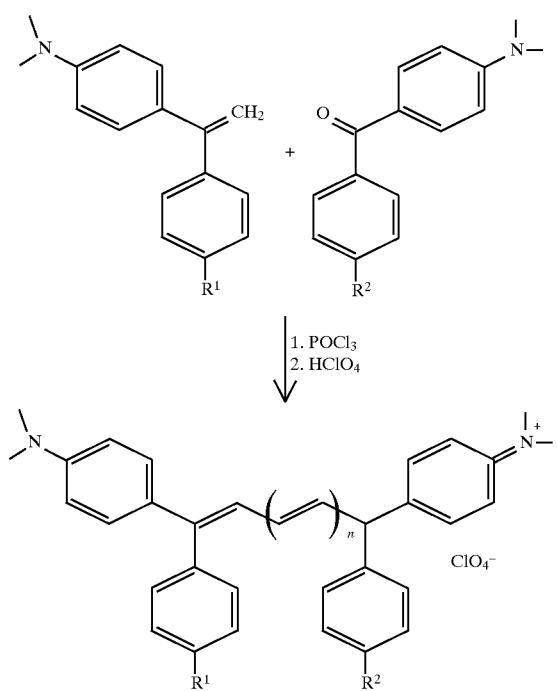

wherein 39–56% yields are obtained if n is 0 and $R_1$ and $R_2$ are H, Cl, or $N(CH_3)_2$.

Similarly, pentamethines (n=1) can be synthesized as follows:

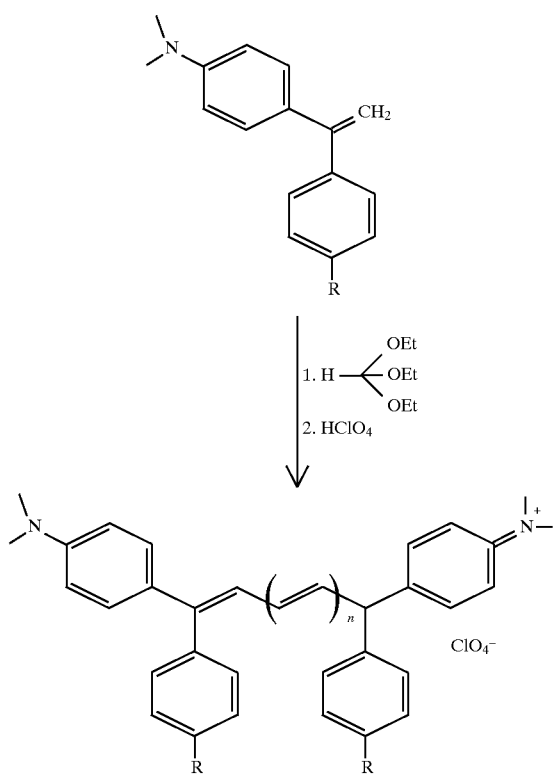

wherein yields of 50–99% may be obtained if n is 1 and R is H, Cl, or $N(CH_3)_2$.

Heptamethines (n=2) can be synthesized as follows:

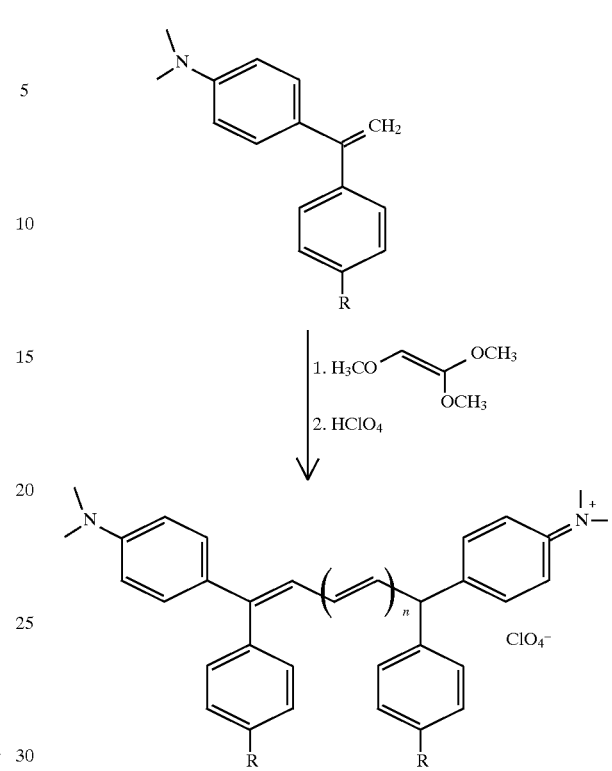

wherein yields of 37–96% can be obtained if n is 2 and R is H, Cl, or $N(CH_3)_2$ Polyethylene glycol (PEG) conjugates of aryl-terminated polymethine dyes include:

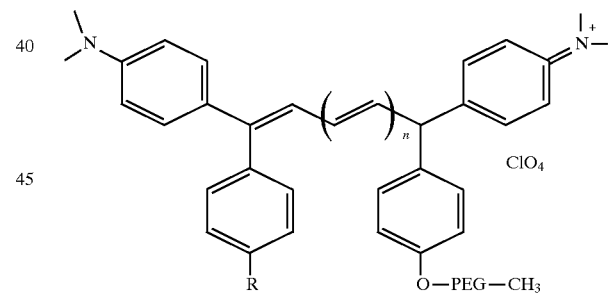

wherein n is 0, 1, or 2 and R includes, but is not limited to H, Cl, Br, I, $N(CH_3)_2$, linker and O—PEG—$OCH_3$.

These PEG containing dyes can be synthesized as follows:

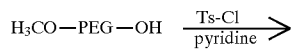
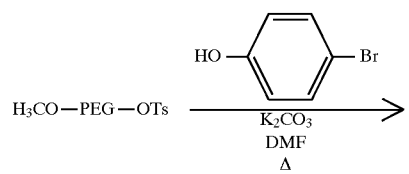

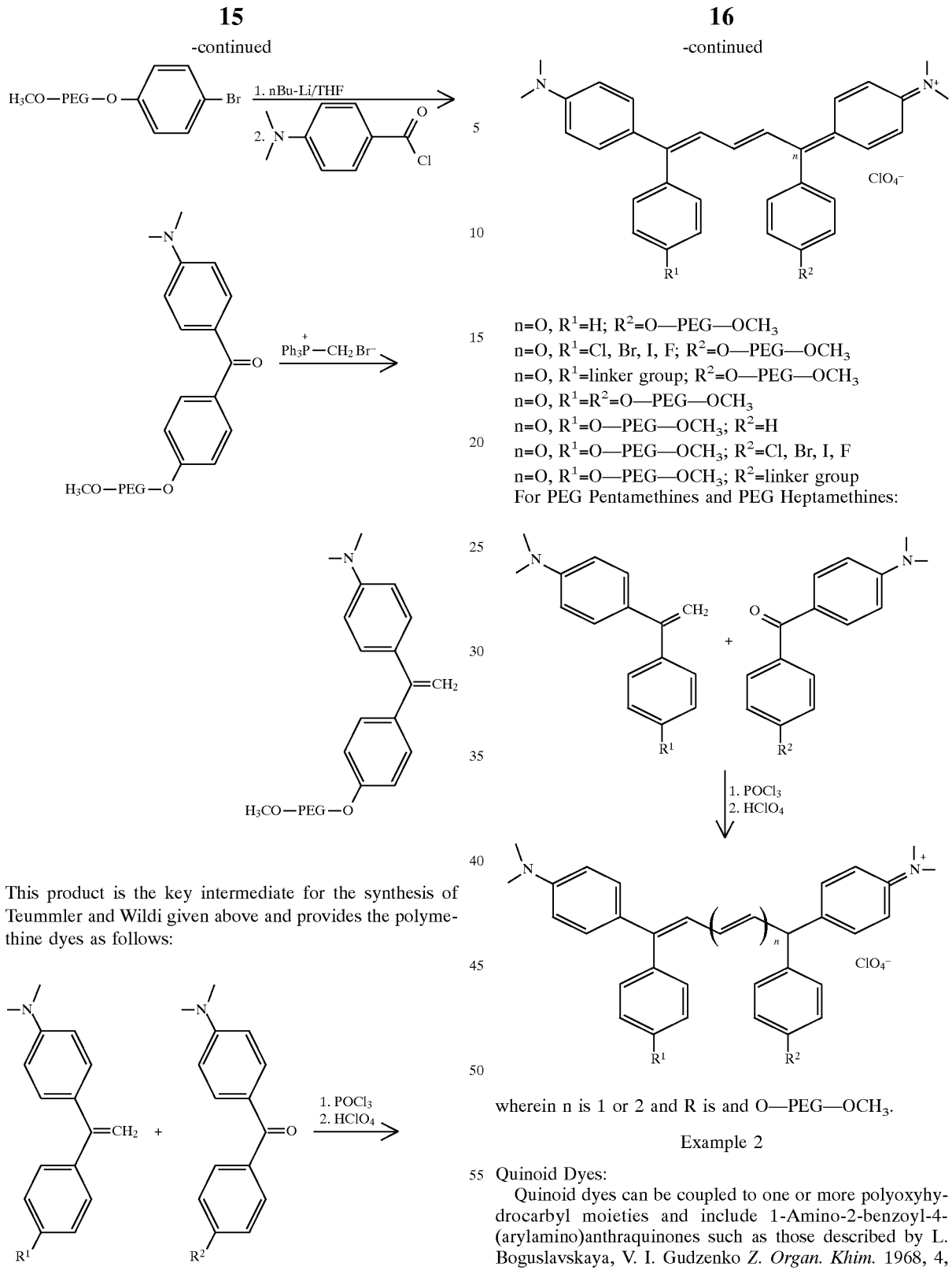

n=0, R¹=H; R²=O—PEG—OCH₃
n=0, R¹=Cl, Br, I, F; R²=O—PEG—OCH₃
n=0, R¹=linker group; R²=O—PEG—OCH₃
n=0, R¹=R²=O—PEG—OCH₃
n=0, R¹=O—PEG—OCH₃; R²=H
n=0, R¹=O—PEG—OCH₃; R²=Cl, Br, I, F
n=0, R¹=O—PEG—OCH₃; R²=linker group
For PEG Pentamethines and PEG Heptamethines:

This product is the key intermediate for the synthesis of Teummler and Wildi given above and provides the polymethine dyes as follows:

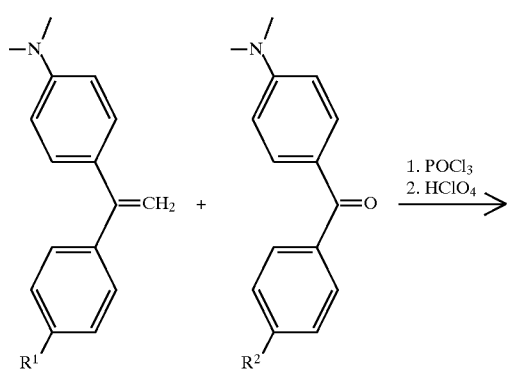

wherein n is 1 or 2 and R is and O—PEG—OCH₃.

Example 2

Quinoid Dyes:

Quinoid dyes can be coupled to one or more polyoxyhydrocarbyl moieties and include 1-Amino-2-benzoyl-4-(arylamino)anthraquinones such as those described by L. Boguslavskaya, V. I. Gudzenko *Z. Organ. Khim.* 1968, 4, 101–104, incorporated herein by reference in its entirety, including any drawings and preferably have the structure:

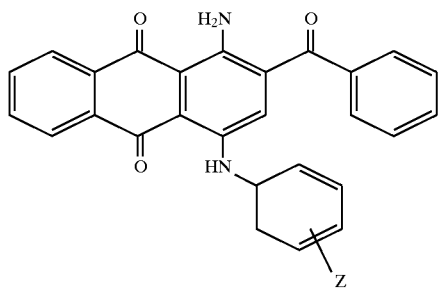

Z = p-OCH₃p-OC₂H₅, p-OH, p-Cl,
p-NO₂, m-Cl, m-CF₃, H, m-NO₂

These compounds have the following spectral properties: $\lambda_{max}$ ranges from ca. 670 to 720 nm and $\epsilon$ ranges from ca. 100,000 to 200,000.

PEG containing conjugates of such compounds can be synthesized as follows:

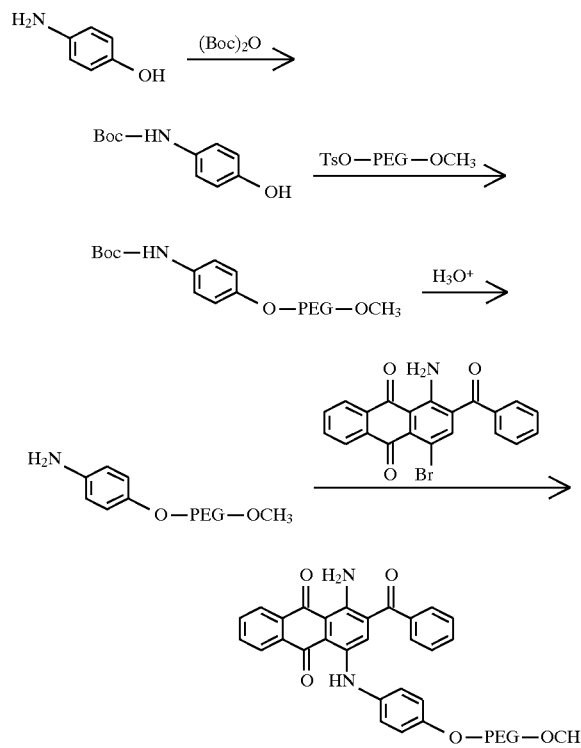

Other quinoid dyes that can be used in the present invention include 6-(Arylamino)napth [2,3,c]acridan-5,8,14-triones such as those described by L. Boguslavskaya, V. I. Gudzenko Z. Organ. Khim. 1968, 4, 101–104 and preferably have the structure:

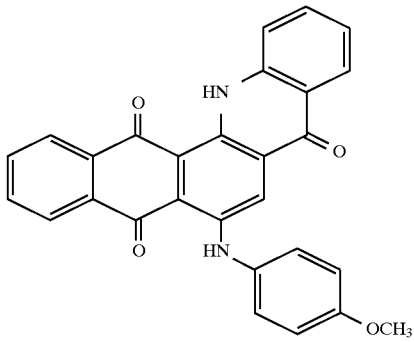

Such compounds have the following spectral properties: $\lambda_{max}$=732 nm. PEG containing conjugates may be synthesized as follows:

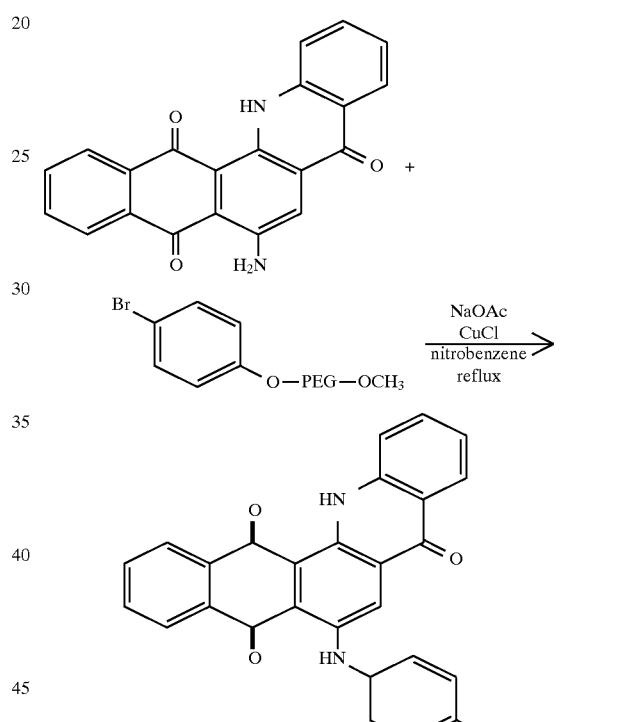

Example 3

Indanthrene Dyes:

Indanthrene dyes may also be coupled to polyoxyhydrocarbyl moieties and include those described in A. Tundo Ann. Chim. (Rome) 1957, 47, 291–298, incorporated herein by reference in its entirety. Such compounds preferably have the general structure:

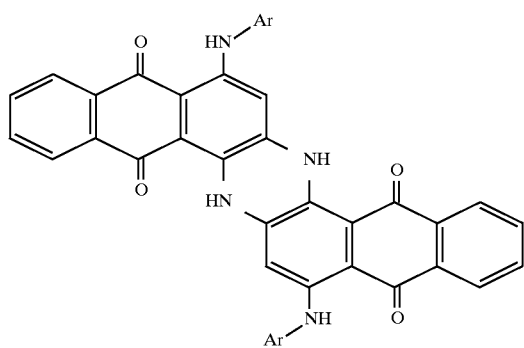

Such compounds have the following spectral properties: $\lambda_{max}$ ranges from ca. 715 nm to 790 nm. log $\epsilon$ ranges from ca. 4.0 to 4.6.

PEG containing conjugates may be synthesized as follows:

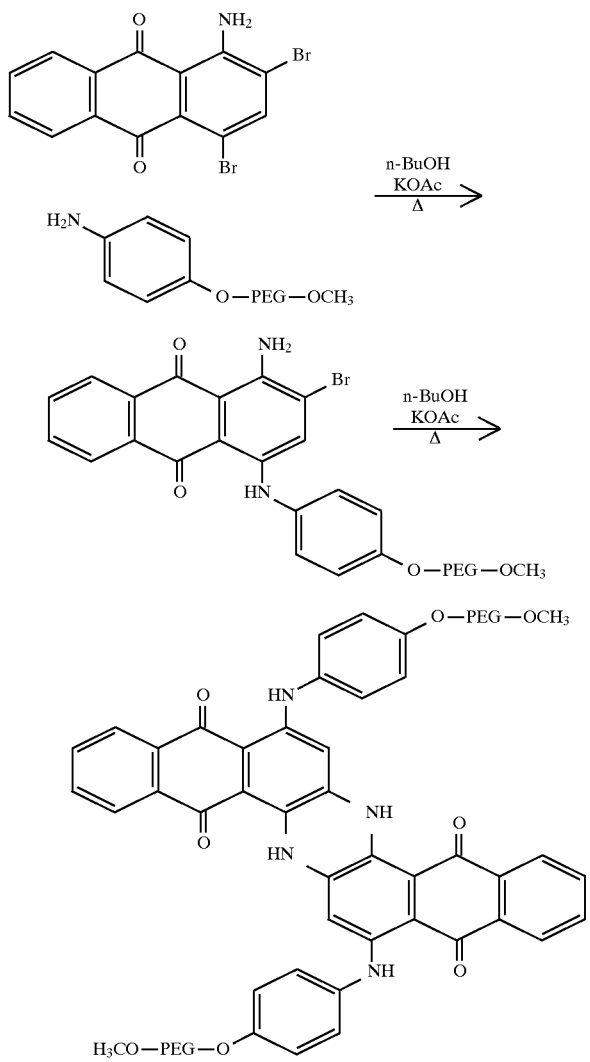

Mixed condensations which incorporate a single PEG residue at position "a" and a suitably functionalized aryl residue at position "b" are also possible using this route.

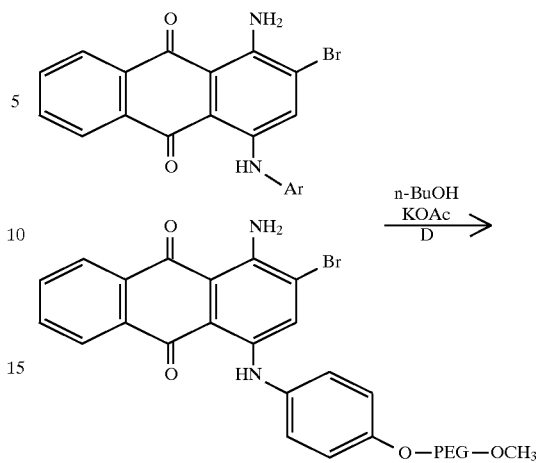

Example 4

1,4-Diaminoanthraquinone-2,3-dicarboxamides:

1,4-Diaminoanthraquinone-2,3-dicarboxamides may also be used and include those described in: *Chemical Abstracts* 1984, 100, 193530n, incorporated herein by reference in its entirety, including any drawings. Such compounds preferably have the structure:

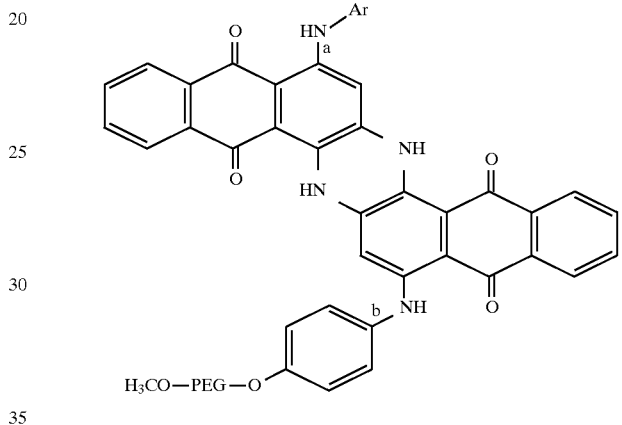

Such compounds have the following spectral properties: for R=n—$C_6H_{13}$, $\lambda_{max}$=763 in the liquid crystalline phase.

PEG conjugates may be synthesized as follows:

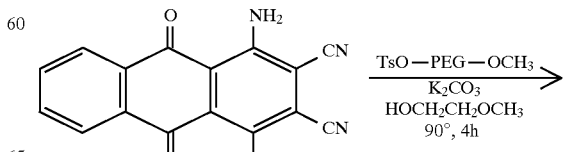

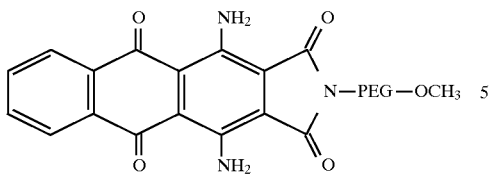

Example 5

Tetraaminoanthraquinones:

Tetraaminoanthraquinones may also be used and include those described in T. Ohyamata, K. Takuma; S. Kuroda, H. Aiga. Eur. Pat. Appl. EP 323,184, 05 Jul. 1989, incorporated herein by reference in its entirety. Such compounds preferably have the structure:

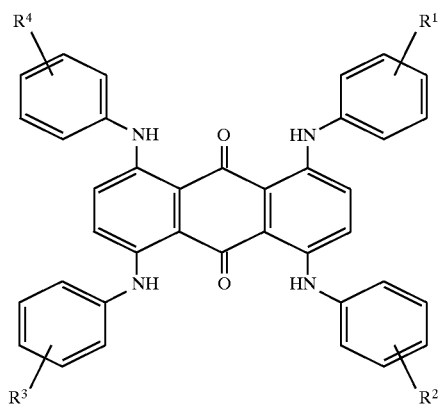

Such compounds have the following spectral properties: for R=alkyl, $l_{max}$=741 in EtOH.

PEG conjugates may be synthesized as follows:

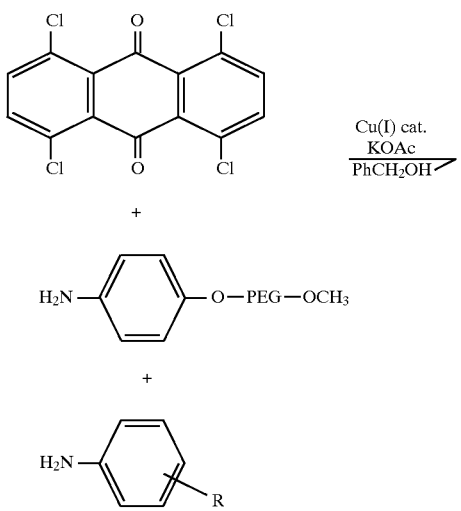

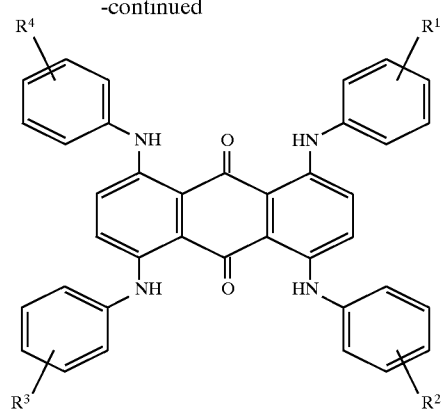

At least one R contains PEG.

Example 6

Azine Dyes

Azine dyes may also be used and preferably have the structure:

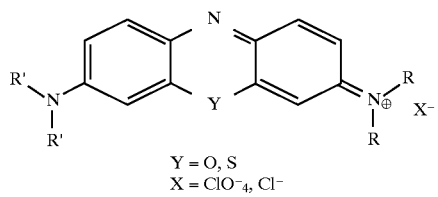

$Y = O, S$
$X = ClO^-_4, Cl^-$

More preferably the dye is Nile Blue A perchlorate and has the structure:

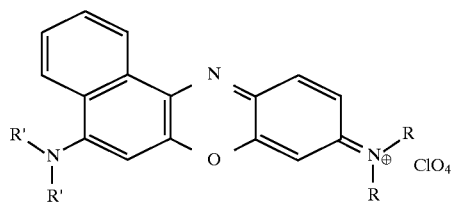

Such compounds have the following spectral properties:

| R | R' | Name | Abs. $\lambda_{max}$ (nm) | Fluor. $\lambda_{max}$ (nm) | $\epsilon \times 10^4$ (L/mol/cm) |
|---|---|---|---|---|---|
| Ethyl | Ethyl | Oxazine 1 | 643 | 658 | 12.30 |
| Ethyl | H | Nile Blue A | 627 | 660 | 7.68 |
| Methyl | Methyl | Methylene Blue | 695* | 885* | NA |
| H | H | Thionin | 695* | 850* | NA |
| Methyl | H | Toluidine Blue | 695* | 848* | NA |

*From: "Laser Dyes", Mitsuo Maeda. For the starred entries, Abs: $\lambda_{max}$ is that of the ruby pumping laser, and Fluoro, lambda max is the lasing wavelength.

PEG conjugates may be synthesized as follows and by using techniques described in Processes of Dye Chemistry (Interscience, New York) 1949.

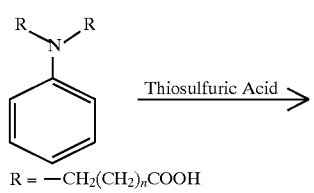

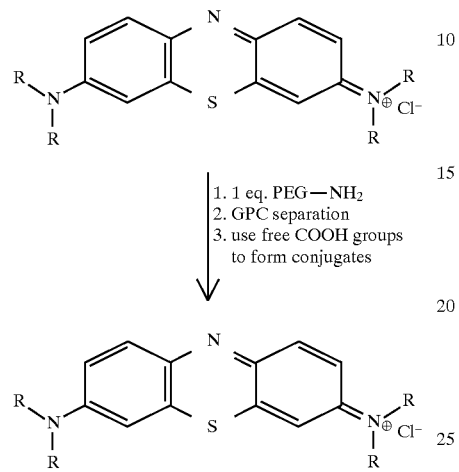

Example 7

Pyrylium and Thiopyryilum Dyes

Pyrylium and Thiopyryilum Dyes may also be used and preferably have the structure:

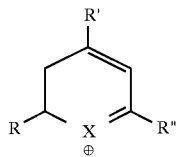

X=O,S

R, R', R"=alkyl, aryl or enol ether

Such compounds may be synthesized as follows and using techniques described in A. T. Balaban, W. Schroth, G. W. Fischer, *Adv. Heterocyclic Chem.* 1969, 10, 241; and A. T. Balaban, A. Dinculescu, G. N. Dorofeenko, G. W. Fischer, A. V. Koblik, V. V. Meqheritskii, W. Schroth "Pyrylium Salts. Syntheses, Reactions and Physical Properties", *Adv. Hetercyclic Chem., Suppl.* 2, Ed. A. R. Katritsky, Academic Press, New York, 1982, both of which are incorporated herein by reference in their entirety, including any drawings.

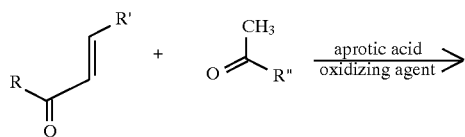

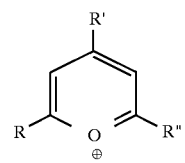

Thiopyrylium analogs are made by treating the pyrylium salts with sodium sulfide.

Such compounds have the following properties:

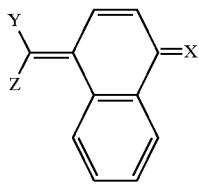

Example 8

Naphthoquinone Methides

Naphthoquinone Methides may also be used and preferably have the structure:

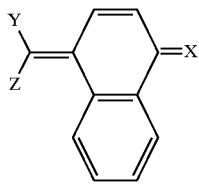

Such compounds may be synthesized as follows and using the techniques described in: *The Chemistry of the Quinoid Compounds*, ed., S. Patai., Y. Kubo, F. Mori, K. Yoshida *Chemistry Letters,* 1987, 1761–1762, incorporated herein by reference in its entirety, including any drawings.

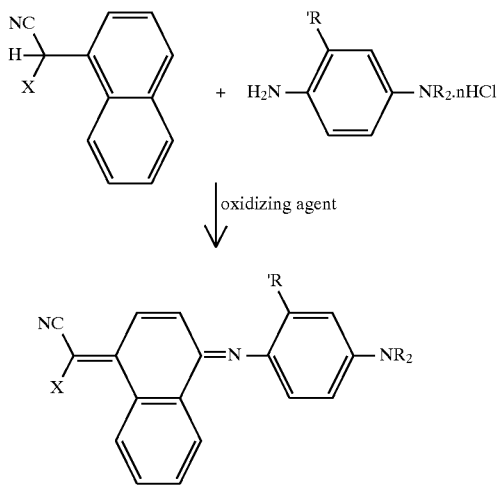

Such compounds have the following properties:

| X | Y | Z | λ(nm) | ε × 10⁴ |
|---|---|---|---|---|
| —N—(2-Me-4-N,N'-Diethylamino-C₆H₃) | CN | CN | 761[a] | 3.1 |
| —N—(4-N,N'-Dimethylamino-C₆H₄) | CN | CN | 722[a] | 2.5 |
| —N—(2-Me-4-N,N'-Diethylamino-C₆H₃) | CN | CONH₂ | 754[a] | 2.9 |

[a]Spectra measured in chloroform.

PEG conjugates could be synthesized following the above route with R or 'R=PEG.

Example 9

Carbazines (also called acridans)

Carbazines may also be used and include those described in *Heterocyclic Compounds* vol. 9 "Acridines," Ed. R. M. Acheson, John Wiley and Sons, Inc., New York, 1973, incorporated herein by reference in its entirety, including any drawings. Such compounds preferably have the structure:

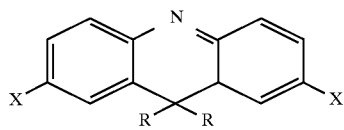

Such compounds may be synthesized as follows:

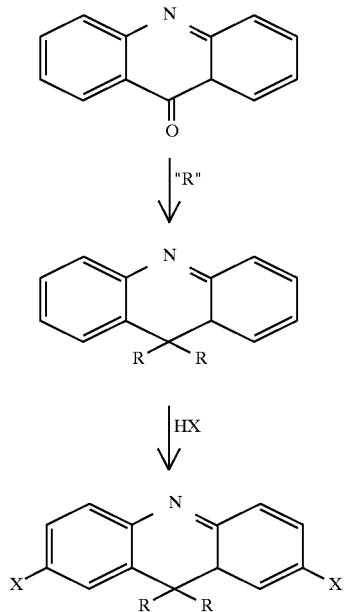

In these reactions one or more of the R groups may be PEG.

Example 10

Non-Specific Binding Tests

Cynanine dyes have a long history as sensitizers in the photographic process. Recently, water soluble cyanine dyes with chemically reactive groups have become commercially available as fluorescent labels. One of these dyes, Cy 5.5 has an absorption maximum at about 680 nm and emits just over 700 nm.

A sample of Cy 5.5 at 1.7 micromolar concentration was kept in digoxin probe diluent for 72 hr. after which time the original active ester form should be converted to the free carboxyl form. Tests for non-specific binding were made with our standard serum panel and showed pronounced effects of serum or serum components on both the intensity and polarization. These effects are manifest as non-linearity in the intensity as a function of concentration (Tables I and II) and in a variation of intensity with the type and concentration of serum component (Table III) with the polarization being elevated by non-specific binding.

TABLE I

Cy 5.5 in Digoxin Diluent

| Concentration nM | Fluorescence Intensity | Milli-polarization Units |
|---|---|---|
| 170 | 416279 | 82.8 |
| 17 | 580613 | outside readability |
| 1.7 | 150069 | 129.0 |
| 0.17 | 38842 | 122.6 |

TABLE II

Cy 5.5 in TDx Buffer

| | | |
|---|---|---|
| 170 | 1074511 | −34.2 |
| 17 | 1338283 | outside readability |
| 1.7 | 150069 | 129.0 |
| 0.17 | 22280 | 130.2 |

TABLE III

Cy 5.5 at 1.7 nM + Additives

| Additive | Intensity | Millipolarization units |
|---|---|---|
| 0.5% BSA | 665960 | 285.5 |
| 5% Bov. Ser. | 555277 | 260.1 |
| 0.25% BGG | 326543 | 191.2 |
| 5% PHS | 608260 | 282.9 |
| 5% PHS | 383004 | 231.9 |

The bis-active ester can be coupled to diisopropyl amine and the binding of this form to serum examined. This test should be indicative of the behavior to be expected from bio-probes made from Cy 5.5. A digoxin probe can be made by reacting the bis-functional dye with an excess of 3-amino-3-deoxydigoxigenin (DIG) so that each dye molecule will be combined with two digoxigenin molecules. This probe can then be tested against the serum panel and against anti-digoxin to determine its properties as digoxin probe.

In order to suppress non-specific binding Cy 5.5 can be coupled to polyethylene glycol monomethyl ether (PEG) as we normally do for phthalocycanines such as those used in making La Jolla Blue. If this bis-reactive form is used then the result will be to couple two PEG molecules to each dye molecule. If the mono-reactive form of the dye is used only one PEG can be coupled so that information on the amount of PEG necessary to achieve the desired degree of suppression will be obtained.

A hybrid molecule containing one digoxigenin molecule and one PEG can be made by first reacting the bis-reactive dye with a limited amount of DIG to obtain a certain of monosubstitution followed by reaction with excess PEG and purification by high performance liquid chromatography (HPLC).

Example 11

Relationship Between Non-Specific Binding and Solubility

Nonspecific binding and water solubility do not necessarily go hand in hand, but instead dye molecules can be monomeric in aqueous solution and yet show powerful nonspecific binding. As an example from our work, the binding constant for a bare phthalocyanine of structure shown as Formula A below reacting with human serum albumin (HSA) was calculated from measurements of transient state fluorescence in potassium phosphate buffer at pH 8.0 with various concentrations of added HSA.

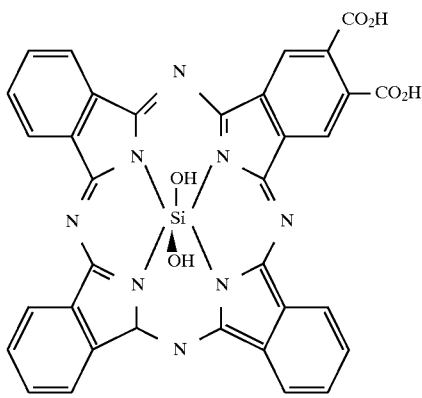

Similar measurements on the dye of Formula A chemically modified by attaching a polyethylene glycol molecule to each of the silanol OH groups to make the dye La Jolla Blue were made in the same buffer and instrument. The results are shown in Table IV below.

TABLE IV

Transient State Fluorescence Intensity and Polarization Measurements on Formula A Dye and on La Jolla Blue with or without Added HSA.
Dye concentration in both cases was 3.1 E-10 M.

| % HSA | Intensity | Polarization (mP) |
|---|---|---|
| | Formula A Dye | |
| 0 | 164696 | 2.4 |
| 0.002 | 105080 | 63.5 |
| 0.02 | 67714 | 153.9 |
| 0.2 | 63672 | 192.8 |
| 2.0 | 78321 | 191.7 |
| 4.0 | 81328 | 201.1 |
| | La Jolla Blue | |
| 0 | 85743 | 1.3 |
| 0.002 | 84887 | 4.8 |
| 0.02 | 82718 | 18.1 |
| 0.2 | 81073 | 20.8 |
| 2.0 | 56085 | 35.8 |
| 4.0 | 71593 | 71.8 |

The data of Table IV can be used to determine the HSA concentration at which the dye is half free and half bound. For the bare dye and for La Jolla Blue this concentration is 3.2 E-7 M and 5.0 E-4 M, respectively, making the binding constants 3E6 and 2E3 $M^{-1}$, respectively. In other words, the introduction of PEG molecules, in this case of formula weight 2000, is capable of decreasing the nonspecific binding constant by a factor of over a thousand.

What is claimed is:

1. A detectably labeled marker component which comprises:
    (a) a fluorophore moiety comprising a luminescent substantially planar molecular structure having an excitation wavelength of at least about 500 nanometers, wherein said fluorophore moiety is a polymethine dye; coupled to
    (b) one or more polyoxyhydrocarbyl moieties, wherein said polyoxyhydrocarbyl moieties are selected from polyethers, polyols, water soluble carbohydrates, water soluble carbohydrate derivatives, and water soluble polymers, wherein said polyoxyhydrocarbyl moieties have a molecular weight of about 200 to 4,000;
    wherein said marker component has decreased non-specific binding to components of serum as compared to the bare fluorophore moiety when it is not coupled to one or more polyoxyhydrocarbyl moieties.

2. A marker component according to claim 1 wherein said fluorophore moiety has an excitation wavelength of about 600 to 800 nanometers.

3. A marker component according to claim 2 wherein said fluorophore moiety has an excitation wavelength of at least 650 nanometers.

4. A marker component according to claim 1 wherein said marker component has substantially similar intensity, decay time and relative magnitudes of the polarized components in the presence and absence of serum.

5. A marker component according to claim 1 wherein said fluorophore moiety alone has a binding constant that is at least 50 times greater than the binding constant of the complete marker component.

6. A marker component according to claim 5 wherein said fluorophore moiety alone has a binding constant that is at least 100 times greater than the binding constant of the complete marker component.

7. A marker component according to claim 6 wherein said fluorophore moiety alone has a binding constant that is at least 500 times greater than the binding constant of the complete marker component.

8. A marker component according to claim 7 wherein said fluorophore moiety alone has a binding constant that is at least 1,000 times greater than the binding constant of the complete marker component.

9. A marker component according to claim 1 wherein said polyoxhydrocarbyl moieties comprise polyethylene glycol or polyethylene glycol derivatives.

10. A marker component according to claim 1 which in the presence of serum components in aqueous solution is characterized by transient state fluorescence emission having parallel and perpendicular components of substantially the same intensities as without serum.

11. A marker component according to claim 1 wherein said polymethine dye is a trimethine.

12. A marker component according to claim 1 wherein said polymethine dye is a pentamethine.

13. A marker component according to claim 1 wherein said polymethine dye is a heptamethine.

14. A marker component according to claim 1, wherein said polymethine dye is an aryl or heteroaryl terminated polymethine dye.

15. A marker component according to claim 14, wherein said aryl or heteroaryl is substituted with one or more substitutents independently selected from the group consisting of methyl, ethyl, chloro, $(CH_2)_3SO^-_3$, and $(CH_2)_4$—$SO^-_3$.

16. A marker component according to claim 14, wherein said aryl or herteroaryl is a bicyclic or tricyclic ring, wherein each ring comprises five or six atoms independently selected from the group consisting of carbon, sulfur and nitrogen, and wherein there are 0, 1 or 2 of said sulfur and/or nitrogen atoms in said ring.

17. A marker component according to claim 14, wherein said polymethine dye is selected from the group consisting of:

3,3'-Diethyl-2,2'-thiadicarbon cyanine iodide;

3,3'-Diethyl-2,2'-thiatricarbon cyanine bromide (iodide);

3,3'-Dimethyl-2,2'-thiatricarbon cyanine iodide;

3,3'-Diethyly-5,5'-dichloro-11-ciphenylamino-10,12-ethylene-thiatricarbocyanine perchlorate;

3'3'-Diethyl-2,2'-oxatricarbon cyanine iodide;

1,1'-Diethyl-2,2'-quinotricarbon cyanine iodide;

1,1'-Diethyl-4,4'-quinocarbon cyanine iodide (cryptocyanine);

1,1'-Diethyl-11-bromo-4,4'quinon dicarbocyanine bromide;

1,1',1"-Triethyl-11-(4'-quinoyl)-4,4'-quinodicarbocyanine diiodide;

1,1'3,3,3',3'-Hexamethyl-2,2'-indotricarbocyanine iodide (HITC);

1,1'3,3,3',3'-Hexamethyl-4,5,4'5'-dibenzo-2,2-indotricarbon cyanine perchlorate;

3,3,3'3'-Tetramethyl-1,1'-bis(4-sulfobutyl)-4,5,4'5'-dibenzo-2,2'-indotricarbon cyanine, sodium salt, (IR-125); and

IR-144.

* * * * *